(12) United States Patent
Carling et al.

(10) Patent No.: US 7,485,640 B2
(45) Date of Patent: Feb. 3, 2009

(54) IMIDAZOPYRAZINONES AS GABA-A RECEPTOR ANXIOLYTICS

(75) Inventors: William Robert Carling, Bishops Stortford (GB); Jose Luis Castro Pineiro, Bishops Stortford (GB); Simon Charles Goodacre, Benington (GB); David James Hallett, Watford (GB); Leslie Joseph Street, Little Hallingbury (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 580 days.

(21) Appl. No.: 10/533,152

(22) PCT Filed: Oct. 29, 2003

(86) PCT No.: PCT/GB03/04685

§ 371 (c)(1),
(2), (4) Date: Apr. 27, 2005

(87) PCT Pub. No.: WO2004/041826

PCT Pub. Date: May 21, 2004

(65) Prior Publication Data

US 2006/0014744 A1 Jan. 19, 2006

(30) Foreign Application Priority Data

Nov. 6, 2002 (GB) .................. 0225923.2
Feb. 4, 2003 (GB) .................. 0302529.3
Feb. 26, 2003 (GB) .................. 0304415.3
Jun. 12, 2003 (GB) .................. 0313646.2

(51) Int. Cl.
*A01N 43/64* (2006.01)
*A01N 43/90* (2006.01)
*A61K 31/53* (2006.01)
*A61K 31/519* (2006.01)
*C07D 253/08* (2006.01)
*C07D 487/00* (2006.01)

(52) U.S. Cl. .................. 514/243; 514/259.5; 544/183; 544/281

(58) Field of Classification Search .................. None
See application file for complete search history.

(56) References Cited

FOREIGN PATENT DOCUMENTS

| DE | 4329970 | * | 6/1994 |
| WO | WO 02 10170 | | 2/2002 |
| WO | WO 02 38568 | | 5/2002 |

OTHER PUBLICATIONS

Dorwald F. A. Side Reactions in Organic Synthesis, 2005, Wiley: VCH, Weinheim p. IX of Preface.*

* cited by examiner

*Primary Examiner*—James O Wilson
*Assistant Examiner*—Jeffrey H Murray
(74) *Attorney, Agent, or Firm*—J. Eric Thies; William Krovatin

(57) ABSTRACT

The present invention discloses a compound of formula I, or a pharmaceutically acceptable salt thereof: (I) wherein —U—V— represents —CH=CH—, or —CH$_2$—CH$_2$—, —N=CH— or —CH=N—; X$^1$ represents hydrogen, halogen, C$_{1-6}$ alkyl, trifluoromethyl or C$_{1-6}$ alkoxy; X$^2$ represents hydrogen or halogen; Y represents a chemical bond, an oxygen atom, or a —NH— or —OCH$_2$— linkage; Z represents an optionally substituted aryl or heteroaryl group; R$_1$ represents hydrocarbon, a heterocyclic group, trifluoromethyl, —SO$_2$R$^a$, —SO$_2$NR$^a$R$^b$, —COR$^a$, —CO$_2$R$^a$ or —CONR$^a$R$^b$; and R$^a$ and R$^b$ independently represent hydrogen, hydrocarbon or a heterocyclic group; pharmaceutical compositions comprising it; its use in methods of treatment; use of it in the manufacture of a medicament for treating and/or preventing anxiety; convulsions or a cognitive disorder; and methods of treatment using it.

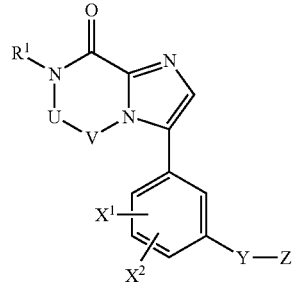

8 Claims, No Drawings

IMIDAZOPYRAZINONES AS GABA-A RECEPTOR ANXIOLYTICS

CROSS REFERENCE TO RELATED APPLICATIONS

This application is a U.S. National Phase application under 35 U.S.C. § 371 of PCT Application No. PCT/GB2003/004685, filed Oct. 29, 2003, which claims priority under 35 U.S.C. § 119 from GB Application No. 0225923.2, filed Nov. 6, 2002, GB Application No. 0302529.3, filed Feb. 4, 2003, GB Application No. 0304415.3, filed Feb. 26, 2003 and GB Application 0313646.2, filed Jun. 12, 2003.

The present invention relates to classes of substituted imidazo-pyrazinone derivatives, substituted imidazotriazine derivatives and purinone derivatives and to their use in therapy. More particularly, this invention is concerned with imidazo[1,2-a]pyrazin-8-one analogues and imidazo[1,2-d]triazin-8-one analogues which are substituted in the 3-position by a substituted phenyl ring, and with purin-6-one analogues which are substituted in the 9-position by a substituted phenyl ring. These compounds are ligands for $GABA_A$ receptors and are therefore useful in the therapy of deleterious neurological complaints.

A description of the theoretical background underlying this invention can be found on pages 1-5 of WO-A-02074773 (Merck Sharp & Dohme Ltd.).

WO 02/10170 describes a class of 3-phenylimidazo[1,2-a]pyrazine derivatives which are stated to be selective ligands for $GABA_A$ receptors, in particular having high affinity for the α2 and/or α3 subunit thereof, and accordingly to be of benefit in the treatment and/or prevention of neurological disorders, including anxiety and convulsions. However, there is no disclosure nor any suggestion in that publication of therapeutic agents based on a 7-substituted imidazo[1,2-a]pyrazin-8-one ring system.

The present invention provides a compound of formula I, or a pharmaceutically acceptable salt thereof:

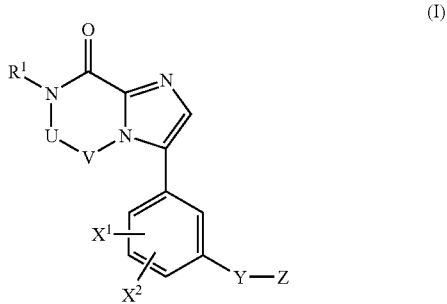

wherein
—U—V— represents —CH=CH—, or —CH$_2$—CH$_2$—, —N=CH— or —CH=N—;
$X^1$ represents hydrogen, halogen, $C_{1-6}$ alkyl trifluoromethyl or $C_{1-6}$ alkoxy;
$X^2$ represents hydrogen or halogen;
Y represents a chemical bond, an oxygen atom, or a —NH— or —OCH$_2$— linkage;
Z represents an optionally substituted aryl or heteroaryl group;
$R^1$ represents hydrocarbon, a heterocyclic group, trifluoromethyl, —SO$_2$R$^a$, —SO$_2$NR$^a$R$^b$, —COR$^a$, —CO$_2$R$^a$ or —CONR$^a$R$^b$; and $R^a$ and $R^b$ independently represent hydrogen, hydrocarbon or a heterocyclic group.

The present invention also provides a compound of formula I as depicted above, or a pharmaceutically acceptable salt thereof, wherein
—U—V— represents —CH=CH—;
Y represents a chemical bond, an oxygen atom, or a —NH— linkage; and
$X^1$, $X^2$, Z and $R^1$ are as defined above.

Definitions of the aryl or heteroaryl group Z, pharmaceutically acceptable salts of the compounds, the terms "hydrocarbon" and "a heterocyclic group" as used herein, suitable alkyl, alkenyl, alkynyl, and cycloalkyl groups, typical examples of $C_{3-7}$ cycloalkyl($C_{1-6}$)alkyl groups, particular indanyl, aryl and aryl($C_{1-6}$)alkyl groups, suitable heterocycloalkyl and heteroaryl groups, the expression "heteroaryl($C_{1-6}$)alkyl", optional substituents on the hydrocarbon and heterocyclic groups and the term "halogen" as used herein can be found on columns 3-5 of U.S. Pat. No. 6,900,215.

General comments about stereochemistry can be found on column 5 of U.S. Pat. No. 6,900,215.

In one embodiment of the compounds according to the present invention, —U—V— represents —CH=CH—.

In another embodiment, —U—V— represents —CH$_2$—CH$_2$—.

Suitable values for the $X^1$ substituent include hydrogen, fluoro, chloro, methyl, trifluoromethyl and methoxy; in particular hydrogen or fluoro; and especially fluoro.

Suitably, $X^1$ represents halogen, $C_{1-6}$ alkyl, trifluoromethyl or $C_{1-6}$ alkoxy. Typical values of $X^1$ include fluoro, chloro, methyl, trifluoromethyl and methoxy, especially fluoro.

Typical values of $X^2$ include hydrogen and fluoro, especially hydrogen.

In a preferred embodiment, Y represents a chemical bond.

In an alternative embodiment, Y represents a —OCH$_2$— linkage.

In another embodiment, Y represents an oxygen atom.

In a further embodiment, Y represents a —NH— linkage.

Selected values for the substituent Z include phenyl, pyridinyl, pyridazinyl, pyrimidinyl, pyrazinyl, furyl, thienyl, oxazolyl, isoxazolyl, thiazolyl, isothiazolyl pyrrolyl, pyrazolyl, imidazolyl, oxadiazolyl, thiadiazolyl, triazolyl and tetrazolyl, any of which groups may be optionally substituted by one or more substituents.

Particular values of Z include phenyl and triazolyl, either of which groups may be optionally substituted by one or more substituents.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH=NOH.

Examples of typical substituents on the group Z include fluoro, chloro, cyano and methyl.

Examples of particular substituents on the group Z include fluoro and cyano, especially cyano.

Detailed values of Z include cyanophenyl (cyano)(fluoro)phenyl, (chloro)(cyano)phenyl, nitrophenyl, methoxyphenyl, methanesulphonyl-phenyl, pyridinyl, fluoro-pyridinyl, difluoro-pyridinyl, (amino)(chloro)pyridinyl, cyano-pyridinyl methyl-pyridinyl, hydroxy-pyridinyl methoxy-pyridinyl oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thienyl-CH=NOH, thiazolyl isothiazolyl, pyrrolyl, pyrazolyl, imidazolyl, triazolyl and methyl-tetrazolyl. Additionally, Z may represent methyl-triazolyl.

Specific values of Z include cyanophenyl, (cyano)(fluoro)phenyl, pyridinyl, difluoro-pyridinyl and cyano-pyridinyl.

Individual values of Z include cyanophenyl, (cyano)fluoro)phenyl, (chloro)(cyano)phenyl and methyl-triazolyl.

In one embodiment, Z represents cyanophenyl, especially 2-cyanophenyl.

In another embodiment, Z represents (cyano)(fluoro)phenyl, especially 2-cyano-4-fluorophenyl. Alternative aspects of this embodiment include 2-cyano-5-fluorophenyl, 2-cyano-6-fluorophenyl and 4-cyano-2-fluorophenyl.

In an additional embodiment, Z represents (chloro)(cyano)phenyl, especially 3-chloro-4-cyanophenyl.

In a further embodiment, Z represents methyl-triazolyl, especially 1-methyl-1H-[1,2,3]triazol-4-yl or 2-methyl-2H-[1,2,4]triazol-3-yl.

Typically, $R^1$ represents hydrocarbon, a heterocyclic group, trifluoromethyl, —$COR^a$ or —$CO_2R^a$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy$(C_{1-6})$alkyl and di$(C_{1-6})$alkylamino$(C_{1-6})$alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Suitable values of $R^1$ include $C_{1-6}$ alkyl, halo$(C_{1-6})$alkyl, dihalo$(C_{1-6})$alkyl, hydroxy$(C_{1-6})$alkyl, dihydroxy$(C_{1-6})$alkyl, $C_{1-6}$ alkoxy$(C_{1-6})$alkyl di$(C_{1-6})$alkoxy$(C_{1-6})$alkyl, cyano$(C_{1-6})$alkyl, $C_{2-6}$ alkoxycarbonyl$(C_{1-6})$alkyl $C_{3-7}$ cycloalkyl, heteroaryl, $C_{1-6}$ alkyl-heteroaryl, heteroaryl$(C_{1-6})$alkyl, trifluoromethyl, formyl, $C_{2-6}$ alkylcarbonyl and $C_{2-6}$ alkoxycarbonyl. Additional values of $R^1$ include trihalo$(C_{1-6})$alkyl and $(C_{1-6})$alkyl-heteroaryl$(C_{1-6})$alkyl.

Representative values of $R^1$ include $C_{1-6}$ alkyl, halo$(C_{1-6})$alkyl, dihalo$(C_{1-6})$alkyl, hydroxy$(C_{1-6})$alkyl and trifluoromethyl.

Particular values of $R^1$ include $C_{1-6}$ alkyl, halo$(C_{1-6})$alkyl, dihalo$(C_{1-6})$alkyl, trihalo$(C_{1-6})$alkyl, heteroaryl$(C_{1-6})$alkyl and $(C_{1-6})$alkyl-heteroaryl$(C_{1-6})$alkyl.

Individual values of $R^1$ include methyl, ethyl, fluoromethyl, difluoromethyl, hydroxymethyl, methoxymethyl, dimethoxymethyl, hydroxyethyl (especially 2-hydroxyethyl), fluoroethyl (especially 2-fluoroethyl), difluoroethyl (especially 2,2-difluoroethyl), dimethoxyethyl (especially 2,2-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, trifluoromethyl, formyl, acetyl and methoxycarbonyl. Additional values of $R^1$ include trifluoroethyl (especially 2,2,2-trifluoroethyl), methyl-triazolylmethyl (especially 2-methyl-2H-[1,2,4]triazol-3-ylmethyl) and pyridinylmethyl (especially pyridin-2-ylmethyl).

Specific values of $R^1$ include methyl, ethyl, fluoroethyl (especially 2-fluoroethyl), difluoroethyl (especially 2,2-difluoroethyl), trifluoroethyl (especially 2,2,2-trifluoroethyl), isopropyl, methyl-triazolylmethyl (especially 2-methyl-2H-[1,2,4]triazol-3-ylmethyl) and pyridinylmethyl (especially pyridin-2-ylmethyl).

In a first embodiment, $R^1$ represents methyl. In a second embodiment, $R^1$ represents ethyl. In a third embodiment, $R^1$ represents fluoroethyl (especially 2-fluoroethyl). In a fourth embodiment, $R^1$ represents difluoroethyl (especially 2,2-difluoroethyl). In a fifth embodiment, $R^1$ represents trifluoroethyl (especially 2,2,2-trifluoroethyl). In a sixth embodiment, $R^1$ represents isopropyl. In a seventh embodiment, $R^1$ represents methyl-triazolylmethyl (especially 2-methyl-2H-[1,2,4]triazol-3-ylmethyl). In an eighth embodiment, $R^1$ represents pyridinylmethyl (especially pyridin-2-ylmethyl). In a favoured embodiment, $R^1$ represents 2-hydroxyprop-2-yl. In another embodiment, $R^1$ represents 2-fluoroprop-2-yl. In an additional embodiment, $R^1$ represents trifluoromethyl.

In one embodiment individual values of $R^1$ when —U—V— is —N=CH— or —CH=N— include methyl, ethyl, fluoromethyl, difluoromethyl, methoxymethyl, dimethoxymethyl, hydroxyethyl (especially 2-hydroxyethyl), fluoroethyl (especially 2-fluoroethyl), difluoroethyl (especially 2,2-difluoroethyl), dimethoxyethyl (especially 2,2-dimethoxyethyl), isopropyl, hydroxypropyl, dihydroxypropyl (especially 1,2-dihydroxyprop-2-yl), cyanopropyl, methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl oxazolyl, methylthiazolyl, methyloxadiazolyl, imidazolylmethyl, triazolylmethyl, trifluoromethyl, formyl, acetyl and methoxycarbonyl.

A particular sub-class of compounds according to the invention is represented by the compounds of formula IIA, and pharmaceutically acceptable salts thereof:

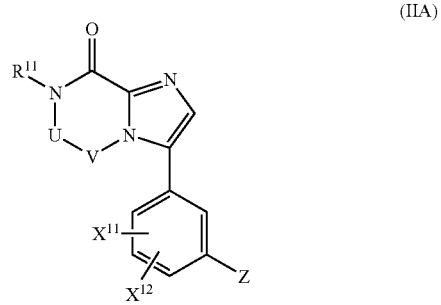

(IIA)

wherein

U, V and Z are as defined above;

$X^{11}$ represents hydrogen, fluoro, chloro, methyl, trifluoromethyl or methoxy;

$X^{12}$ represents hydrogen or fluoro; and $R^{11}$ represents $C_{1-6}$ alkyl, halo$(C_{1-6})$alkyl, dihalo$(C_{1-6})$alkyl, trihalo$(C_{1-6})$alkyl, hydroxy$(C_{1-6})$alkyl, dihydroxy$(C_{1-6})$alkyl, $C_{1-6}$ alkoxy$(C_{1-6})$alkyl, di$(C_{1-6})$alkoxy$(C_{1-6})$alkyl, cyano$(C_{1-6})$alkyl $C_{2-6}$ alkoxycarbonyl$(C_{1-6})$alkyl, $C_{3-7}$ cycloalkyl, heteroaryl, $C_{1-6}$ alkyl-heteroaryl heteroaryl$(C_{1-6})$alkyl, $(C_{1-6})$allyl-heteroaryl$(C_{1-6})$allyl, trifluoromethyl, formyl, $C_{2-6}$ alkylcarbonyl or $C_{2-6}$ alkoxycarbonyl.

The present invention also provides a compound of formula IIA as depicted above, or a pharmaceutically acceptable salt thereof, wherein —U—V— represents —CH=CH—;

$R^{11}$ represents $C_{1-6}$ alkyl, halo$(C_{1-6})$alkyl, dihalo$(C_{1-6})$alkyl, hydroxy$(C_{1-6})$alkyl, dihydroxy$(C_{1-6})$alkyl, $C_{1-6}$ alkoxy $(C_{1-6})$alkyl, di$(C_{1-6})$alkoxy$(C_{1-6})$alkyl, cyano$(C_{1-6})$alkyl, $C_{2-6}$ alkoxycarbonyl$(C_{1-6})$alkyl, $C_{3-7}$ cycloalkyl, heteroaryl, $C_{1-6}$ alkyl-heteroaryl, heteroaryl$(C_{1-6})$alkyl, trifluoromethyl, formyl, $C_{2-6}$ alkylcarbonyl or $C_{2-6}$ alkoxycarbonyl; and Z, $X^{11}$ and $X^{12}$ are as defined above.

Suitable values of $X^{11}$ include hydrogen and fluoro, especially fluoro.

Typical values of $X^{11}$ include fluoro, chloro, methyl, trifluoromethyl and methoxy.

A particular value of $X^{11}$ is fluoro.

In a favoured embodiment, $X^{12}$ represents hydrogen. In another embodiment, $X^{12}$ represents fluoro.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl$(C_{1-6})$alkyl, this group is suitably imidazolylmethyl or triazolylmethyl. Additionally, the heteroaryl$(C_{1-6})$alkyl group $R^{11}$ may be pyridinylmethyl.

Representative values of $R^{11}$ include $C_{1-6}$ alkyl, halo$(C_{1-6})$alkyl dihalo$(C_{1-6})$alkyl, hydroxy$(C_{1-6})$alkyl and trifluoromethyl.

Particular values of $R^{11}$ include $C_{1-6}$ alkyl, halo$(C_{1-6})$alkyl, dihalo$(C_{1-6})$alkyl, trihalo$(C_{1-6})$alkyl, heteroaryl$(C_{1-6})$alkyl and $(C_{1-6})$alkyl-heteroaryl$(C_{1-6})$alkyl.

Individual values of $R^{11}$ include methyl, ethyl, fluoromethyl, difluoromethyl, hydroxymethyl, methoxymethyl, dimethoxymethyl, hydroxyethyl (especially 2-hydroxyethyl), fluoroethyl (especially 2-fluoroethyl), difluoroethyl (especially 2,2-difluoroethyl), dimethoxyethyl (especially 2,2-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, trifluoromethyl, formyl, acetyl and methoxycarbonyl. Additional values of $R^{11}$ include trifluoroethyl (especially 2,2,2-trifluoroethyl), methyl-triazolylmethyl (especially 2-methyl-2H-[1,2,4]triazol-3-ylmethyl) and pyridinylmethyl (especially pyridin-2-ylmethyl).

Specific values of $R^{11}$ include methyl, ethyl, fluoroethyl (especially 2-fluoroethyl), difluoroethyl (especially 2,2-difluoroethyl), trifluoroethyl (especially 2,2,2-trifluoroethyl), isopropyl, methyl-triazolylmethyl (especially 2-methyl-2H-[1,2,4]triazol-3-ylmethyl) and pyridinylmethyl (especially pyridin-2-ylmethyl).

In a first embodiment, $R^{11}$ represents methyl. In a second embodiment, $R^{11}$ represents ethyl. In a third embodiment, $R^{11}$ represents fluoroethyl (especially 2-fluoroethyl). In a fourth embodiment, $R^{11}$ represents difluoroethyl (especially 2,2-difluoroethyl). In a fifth embodiment, $R^{11}$ represents trifluoroethyl (especially 2,2,2-trifluoroethyl). In a sixth embodiment, $R^{11}$ represents isopropyl. In a seventh embodiment, $R^{11}$ represents methyl-triazolylmethyl (especially 2-methyl-2H-[1,2,4]triazol-3-ylmethyl). In an eighth embodiment, $R^{11}$ represents pyridinylmethyl (especially pyridin-2-ylmethyl). In a favoured embodiment, $R^{11}$ represents 2-hydroxyprop-2-yl. In another embodiment, $R^{11}$ represents 2-fluoroprop-2-yl. In an additional embodiment, $R^{11}$ represents trifluoromethyl.

When —U—V— is —N=CH— or —CH=N— individual values of $R^{11}$ include methyl, ethyl fluoromethyl, difluoromethyl, methoxymethyl, dimethoxymethyl, hydroxyethyl (especially 2-hydroxyethyl), fluoroethyl (especially 2-fluoroethyl), difluoroethyl (especially 2,2-difluoroethyl), dimethoxyethyl (especially 2,2-dimethoxyethyl), isopropyl, hydroxypropyl, dihydroxypropyl (especially 1,2-dihydroxyprop-2-yl), cyanopropyl, methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl methyloxadiazolyl imidazolylmethyl, triazolylmethyl, trifluoromethyl, formyl, acetyl and methoxycarbonyl.

One representative subset of the compounds of formula IIA above is represented by the compounds of formula IIB, and pharmaceutically acceptable salts thereof:

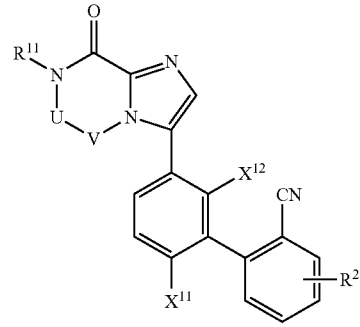

(IIB)

wherein U, V, $X^{11}$, $X^{12}$ and $R^{11}$ are as defined above; and $R^2$ represents hydrogen or fluoro.

In one embodiment, $R^2$ is hydrogen.

In another embodiment, $R^2$ is fluoro, in which case the fluorine atom $R^2$ is favourably attached to the phenyl ring at the 4-, 5- or 6-position (relative to the cyano group at position 2).

Another representative subset of the compounds of formula IIA above is represented by the compounds of formula IIC, and pharmaceutically acceptable salts thereof:

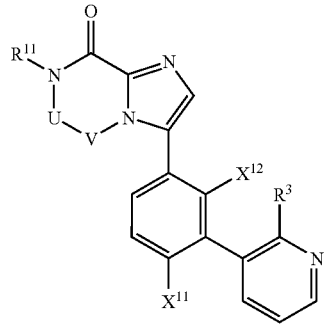

(IIC)

wherein U, V, $X^{11}$, $X^{12}$ and $R^{11}$ are as defined above; and $R^3$ represents hydrogen, fluoro, cyano or methyl.

In one embodiment, $R^3$ is hydrogen.

In an additional embodiment, $R^3$ is fluoro.

In another embodiment, $R^3$ is cyano.

In a further embodiment, $R^3$ is methyl.

A further representative subset of the compounds of formula IIA above is represented by the compounds of formula IID, and pharmaceutically acceptable salts thereof:

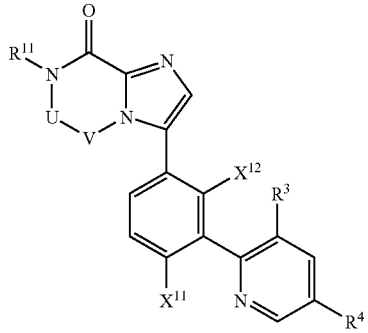

(IID)

wherein U, V, $X^{11}$, $X^{12}$, $R^3$ and $R^{11}$ are as defined above; and $R^4$ represents hydrogen or fluoro.

Suitably, $R^4$ represents hydrogen.

In another embodiment, $R^4$ represents fluoro.

The present invention also provides a compound of formula IIB, IIC or IID as depicted above, or a pharmaceutically acceptable salt thereof, wherein
—U—V— represents —CH=CH—; and
$X^{11}$, $X^{12}$, $R^2$, $R^3$, $R^4$ and $R^{11}$ are as defined above.

Specific compounds within the scope of the present invention include:
2'-fluoro-5'-(7-methyl-8-oxo-7,8-dihydroimidazo[1,2-a]pyrazin-3-yl)-biphenyl-2-carbonitrile;
5'-(7-ethyl-8-oxo-7,8-dihydroimidazo[1,2-a]pyrazin-3-yl)-2'-fluorobiphenyl-2-carbonitrile;
2'-fluoro-5'-[7-(2-fluoroethyl)-8-oxo-7,8-dihydroimidazo[1,2-a]pyrazin-3-yl]biphenyl-2-carbonitrile;
5'-[7-(2,2-difluoroethyl)-8-oxo-7,8-dihydroimidazo[1,2-a]pyrazin-3-yl]-2'-fluorobiphenyl-2-carbonitrile;
4,2'-difluoro-5'-(7-methyl-8-oxo-7,8-dihydroimidazo[1,2-a]pyrazin-3-yl)-biphenyl-2-carbonitrile;
4,2'-difluoro-5'-(7-ethyl-8-oxo-7,8-dihydroimidazo[1,2-a]pyrazin-3-yl)-biphenyl-2-carbonitrile;
4,2'-difluoro-5'-[7-(2,2-difluoroethyl)-8-oxo-7,8-dihydroimidazo[1,2-a]pyrazin-3-yl]biphenyl-2-carbonitrile;
4,2'-difluoro-5'-[7-(1-methylethyl)-8-oxo-7,8-dihydroimidazo[1,2-a]pyrazin-3-yl]biphenyl-2-carbonitrile;
3-chloro-2'-fluoro-5'-(7-methyl-8-oxo-7,8-dihydroimidazo[1,2-a]pyrazin-3-yl)biphenyl-4-carbonitrile;
4,2'-difluoro-5'-[7-(2-fluoroethyl)-8-oxo-7,8-dihydroimidazo[1,2-a]pyrazin-3-yl]biphenyl-2-carbonitrile;
4'-fluoro-3'-(7-methyl-8-oxo-7,8-dihydroimidazo[1,2-a]pyrazin-3-yl)-biphenyl-2-carbonitrile;
5'-fluoro-3'-(7-methyl-8-oxo-7,8-dihydroimidazo[1,2-a]pyrazin-3-yl)-biphenyl-2-carbonitrile;
2,2'-difluoro-5'-(7-methyl-8-oxo-7,8-dihydroimidazo[1,2-a]pyrazin-3-yl)-biphenyl-4-carbonitrile;
4,2'-difluoro-5'-[7-(2,2,2-trifluoroethyl)-8-oxo-7,8-dihydroimidazo[1,2-a]pyrazin-3-yl]biphenyl-2-carbonitrile;
4,2'-difluoro-5'-[7-(2-methyl-2H-[1,2,4]triazol-3-ylmethyl)-8-oxo-7,8-dihydroimidazo[1,2-a]pyrazin-3-yl]biphenyl-2-carbonitrile;
3-[4-fluoro-3-(1-methyl-1H-[1,2,3]triazol-4-ylmethoxy)phenyl]-7-methyl-7H-imidazo[1,2-a]pyrazin-8-one;
3-[4-fluoro-3-(2-methyl-2H-[1,2,4]triazol-3-ylmethoxy)phenyl]-7-methyl-7H-imidazo[1,2-a]pyrazin-8-one;
7-ethyl-3-[4-fluoro-3-(2-methyl-2H-[1,2,4]triazol-3-ylmethoxy)phenyl]-7H-imidazo[1,2-a]pyrazin-8-one;
4,2'-difluoro-5'-[8-oxo-7-(pyridin-2-ylmethyl)-7,8-dihydroimidazo[1,2-a]pyrazin-3-yl)biphenyl-2-carbonitrile;
4,2'-difluoro-5'-(7-methyl-8-oxo-5,6,7,8-tetrahydroimidazo[1,2-a]pyrazin-3-yl)biphenyl-2-carbonitrile;
4,2'-difluoro-5'-(7-ethyl-8-oxo-5,6,7,8-tetrahydroimidazo[1,2-a]pyrazin-3-yl)biphenyl-2-carbonitrile;
5,2'-difluoro-5'-(7-ethyl-8-oxo-5,6,7,8-tetrahydroimidazo[1,2-a]pyrazin-3-yl)biphenyl-2-carbonitrile;
6,2'-difluoro-5'-(7-ethyl-8-oxo-5,6,7,8-tetrahydroimidazo[1,2-a]pyrazin-3-yl)biphenyl-2-carbonitrile;
6,2'-difluoro-5'-(7-methyl-8-oxo-7,8-dihydroimidazo[1,2-a]pyrazin-3-yl)-biphenyl-2-carbonitrile;
6,2'-difluoro-5'-(7-ethyl-8-oxo-7,8-dihydroimidazo[1,2-a]pyrazin-3-yl)-biphenyl-2-carbonitrile;
5,2'-difluoro-5'-(7-methyl-8-oxo-5,6,7,8-tetrahydroimidazo[1,2-a]pyrazin-3-yl)biphenyl-2-carbonitrile;
4,2'-difluoro-5'-[8-oxo-7-(pyridin-2-ylmethyl)-5,6,7,8-tetrahydro-imidazo[1,2-a]pyrazin-3-yl)biphenyl-2-carbonitrile;
6,2'-difluoro-5'-(7-methyl-8-oxo-5,6,7,8-tetrahydroimidazo[1,2-a]pyrazin-3-yl)biphenyl-2-carbonitrile;

and pharmaceutically acceptable salts thereof

Also provided is:
4,2'-difluoro-5'-(7-methyl-8-oxo-7,8-dihydroimidazo[1,2-d][1,2,4]triazin-3-yl)biphenyl-2-carbonitrile;

and pharmaceutically acceptable salts thereof.

Also provided is:
3'-(1-methyl-6-oxo-1,6-dihydropurin-9-yl)biphenyl-2-carbonitrile;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

Details of the binding affinity of the claimed compounds, their potentation of the GABA $EC_{20}$ response, measurement of anxiolytic and anticonvulsant activity, and pharmaceutical compositions can be found on pages 27-30 of WO-A-02074773.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

Unit dosage forms comprising the claimed compounds contain from 0.1 to about 500 mg of the active ingredient of the present invention. Typical unit dosage forms contain from 1 to 100 mg, for example 1, 2, 5, 10, 25, 50 or 100 mg, of the active ingredient.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises attachment of the $R^1$ moiety to a compound of formula III:

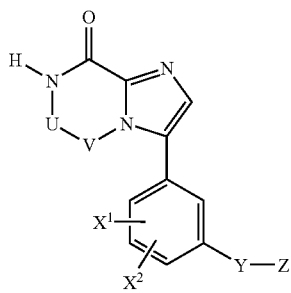

wherein U, V, $X^1$, $X^2$, Y and Z are as defined above; by conventional alkylation or acylation methods.

For instance, where $R^1$ in the compounds of formula I above represents an optionally substituted $C_{1-6}$ alkyl group, the moiety $R^1$ may be attached by treating the appropriate compound of formula III with a suitable alkyl halide, e.g. iodomethane, iodoethane, 1-bromo-2-fluoroethane, 2-bromo-1,1-difluoroethane, 1-iodo-2,2,2-trifluoroethane or 2-bromopropane, typically in the presence of a base such as sodium hydride. Similarly, where $R^1$ represents an optionally substituted heteroaryl($C_{1-6}$)alkyl group, the moiety $R^1$ may be attached by reacting the appropriate compound of formula III with a suitable alkylating agent, e.g. 3-chloromethyl-2-methyl-2H-[1,2,4]triazole or 2-chloromethylpyridine, typically in the presence of a base such as sodium hydride. Alternatively, where $R^1$ in the compounds of formula I above represents methyl, the methyl group $R^1$ may be attached by treating the appropriate compound of formula III with a strong base such as hexamethyldisilazane, followed by chloro(chloromethyl)dimethylsilane; and subsequently treating the compound thereby obtained with cesium fluoride.

Except where $X^1$ and $X^2$ both simultaneously represent hydrogen, the compounds of formula III above are novel compounds and represent a further feature of the present invention.

The compounds of formula III may suitably be prepared from the appropriate methoxy-substituted compound of formula IV:

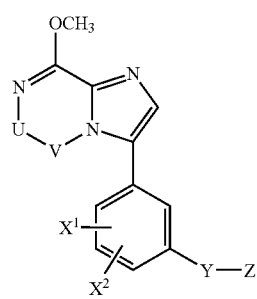

wherein U, V, $X^1$, $X^2$, Y and Z are as defined above; by treatment with hydrogen bromide, typically in acetic acid.

In another procedure, the compounds in accordance with the present invention may be prepared by a process which comprises reacting a compound of formula V with a compound of formula VI:

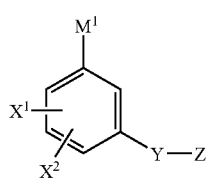

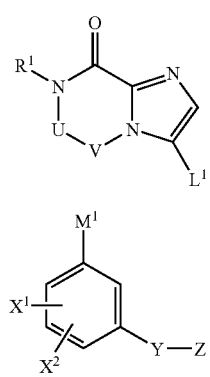

wherein U, V, $X^1$, $X^2$, Y, Z and $R^1$ are as defined above, $L^1$ represents a suitable leaving group, and $M^1$ represents a boronic acid moiety —B(OH)$_2$ or a cyclic ester thereof formed with an organic diol, e.g. pinacol, 1,3-propanediol or neopentyl glycol, or $M^1$ represents —Sn(Alk)$_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds V and VI is suitably palladium(II) acetate, in which case the reaction is typically accomplished in the presence of triphenylphosphine. The reaction is conveniently carried out at an elevated temperature in a solvent such as 1,4-dioxane, typically in the presence of sodium carbonate.

The intermediates of formula V may be prepared by attaching the $R^1$ moiety to a compound of formula VII:

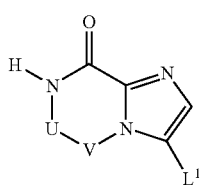

wherein U, V and L¹ are as defined above; under conditions analogous to those described above for attachment of the R¹ moiety to a compound of formula III.

The intermediates of formula VII may be prepared from the appropriate methoxy-substituted precursor of formula VIII:

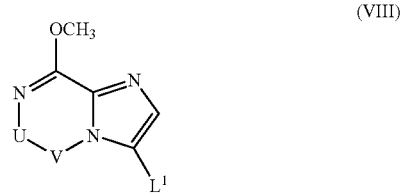

(VIII)

wherein U, V and L¹ are as defined above; by treatment with hydrogen bromide, typically in acetic acid.

In a further procedure, the compounds in accordance with the present invention may be prepared by a process which comprises reacting a compound of formula IX with a compound of formula X:

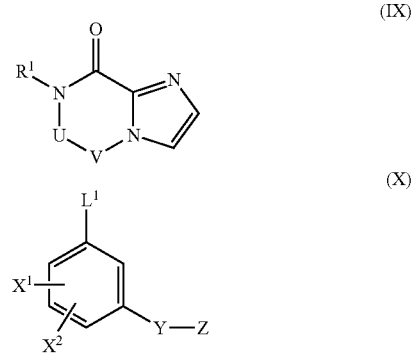

(IX)

(X)

wherein U, V, X¹, X², Y, Z, R¹ and L¹ are as defined above; in the presence of a transition metal catalyst.

The transition metal catalyst of use in the reaction between compounds IX and X is suitably palladium(II) acetate, in which case the reaction is typically accomplished in the presence of triphenylphosphine. The reaction is conveniently carried out at an elevated temperature in a solvent such as N,N-dimethylacetamide, typically in the presence of potassium acetate.

The intermediates of formula IX where —U—V— is —N=C— may suitably be prepared by attachment of the R¹ moiety to the compound of formula XI:

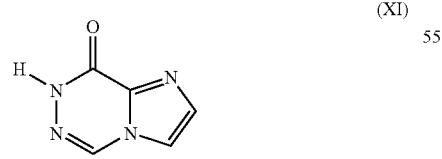

(XI)

by conventional alkylation or acylation methods.

For instance, where R¹ in the compounds of formula I above represents an optionally substituted $C_{1-6}$ alkyl group, the moiety R¹ may be attached by treating the appropriate compound of formula IX with a suitable alkyl halide, e.g. iodomethane, iodoethane, 1-bromo-2-fluoroethane or 2-bromo-1,1-difluoroethane, typically in the presence of a base such as sodium hydride. Alternatively, where R¹ in the compounds of formula I above represents methyl, the methyl group R¹ may be attached by treating the appropriate compound of formula IX with a strong base such as hexamethyldisilazane, followed by chloro(chloromethyl)-dimethylsilane; and subsequently treating the compound thereby obtained with cesium fluoride.

The intermediate of formula XI may be prepared by reacting the compound of formula XII:

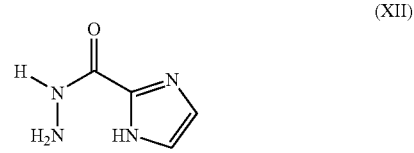

(XII)

with N,N-dimethylformamide dimethyl acetal, typically by heating in Dowtherm A.

The intermediate of formula XII may be obtained from the process described in EP-A-0713876.

The compounds in accordance with the present invention particularly those in which —U—V— is —CH=N—, may alternatively be prepared by a process which comprises reacting a compound of formula XIII:

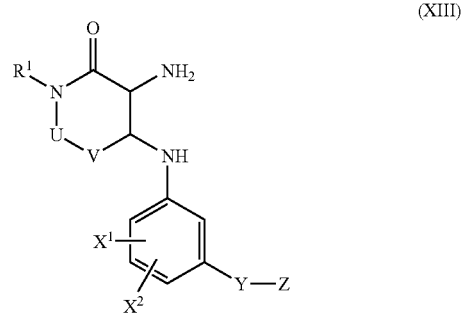

(XIII)

wherein U, V, X¹, X², Y, Z and R¹ are as defined above; with formic acid.

The reaction is conveniently accomplished by stirring the reactants at an elevated temperature, typically at the reflux temperature of the reaction mixture.

The intermediates of formula XIII may be prepared by reduction of a compound of formula XIV:

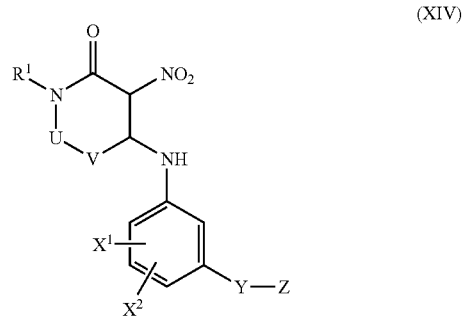

(XIV)

wherein U, V, X¹, X², Y, Z and R¹ are as defined above.

The reduction is conveniently effected by treating compound XIV with a reducing agent, e.g. tin(II) chloride, typically at an elevated temperature in a suitable solvent, for example a mixture of ethanol and tetrahydrofuran.

The intermediates of formula XIV may be prepared by reacting a compound of formula XV with a compound of formula XVI:

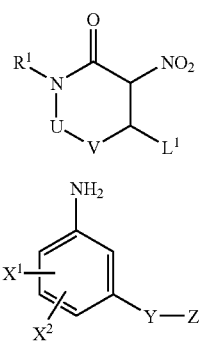

(XV)

(XVI)

wherein U, V, $X^1$, $X^2$, Y, Z and $R^1$ are as defined above, and $L^1$ represents a suitable leaving group.

The leaving group $L^1$ is typically a halogen atom, e.g. chloro.

The reaction between compounds XV and XVI is conveniently effected by heating the reactants, to a temperature typically in the region of 90° C., in the presence of a base such as triethylamine, in a solvent such as dimethylsulfoxide.

In another procedure, the compounds according to the present invention, particularly those in which —U—V— is —CH=N—, in which Y represents a chemical bond may be prepared by a process which comprises reacting a compound of formula XVII with a compound of formula XVIII:

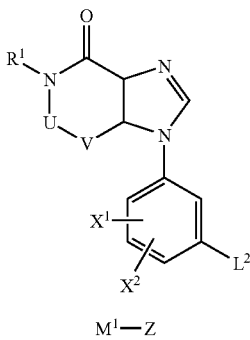

(XVII)

(XVIII)

wherein U, V, $X^1$, $X^2$, Z and $R^1$ are as defined above, $L^2$ represents a suitable leaving group, and $M^1$ represents a boronic acid moiety —B(OH)$_2$ or a cyclic ester thereof formed with an organic diol, e.g. pinacol, 1,3-propanediol or neopentyl glycol, or $M^1$ represents —Sn(Alk)$_3$ in which Alk represents a $C_{1-6}$ alkyl group, typically n-butyl; in the presence of a transition metal catalyst.

In the compounds of formula XVII above, the leaving group $L^2$ is typically trifluoromethanesulfonyloxy (triflyloxy); or a halogen atom, e.g. bromo.

The transition metal catalyst of use in the reaction between compounds XVII and XVIII is suitably tetrakis(triphenylphosphine)-palladium(0). The reaction is conveniently carried out at an elevated temperature in a solvent such as N,N-dimethylacetamide, 1,2-dimethoxyethane, 1,4-dioxane or tetrahydrofuran, advantageously in the presence of potassium phosphate, copper(I) iodide, sodium carbonate or cesium carbonate. Alternatively, the transition metal catalyst employed may be tris(dibenzylideneacetone)dipalladium(0), in which case the reaction is conveniently effected at an elevated temperature in a solvent such as 1,4-dioxane, typically in the presence of tri-tert-butylphosphine and potassium phosphate.

Alternatively, the compounds according to the present invention, particularly those in which —U—V— is —CH=N—, in which Y represents a chemical bond may be prepared by a process which comprises reacting a compound of formula XIX with a compound of formula XX:

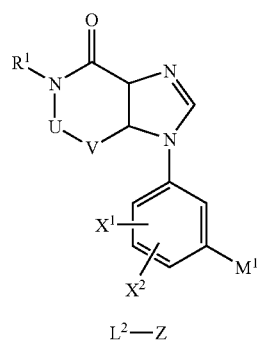

(XIX)

(XX)

wherein U, V, $X^1$, $X^2$, Z, $R^1$, $L^2$ and $M^1$ are as defined above; in the presence of a transition metal catalyst; under conditions analogous to those described above for the reaction between compounds XVII and XVIII.

In an additional procedure, the compounds according to the present invention, particularly those in which —U—V— is —CH=N—, in which Y represents an oxygen atom may be prepared by a process which comprises reacting a compound of formula XX as defined above with a compound of formula XXI:

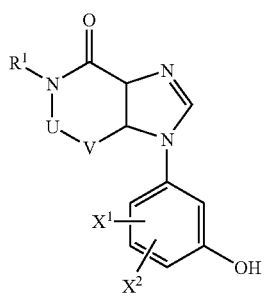

(XXI)

wherein U, V, $X^1$, $X^2$ and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention, particularly those in which —U—V— is —CH=N—, in which Y represents a —NH— linkage may be prepared by a process which comprises reacting a compound of formula XX as defined above with a compound of formula XXII:

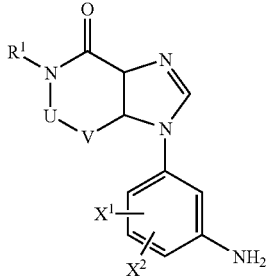

(XXII)

wherein U, V, $X^1$, $X^2$ and $R^1$ are as defined above.

In relation to the reaction between compounds XX and XXII, the leaving group $L^2$ in the compounds of formula XX may suitably represent fluoro.

The reaction between compounds XX and XXII is conveniently carried out by heating the reactants, typically at a temperature in the region of 120° C., in a solvent such as N,N-dimethylformamide.

Where $M^1$ in the intermediates of formula XVIII and XIX above represents a boronic acid moiety —$B(OH)_2$ or a cyclic ester thereof formed with pinacol or neopentyl glycol, the relevant compound XVIII or XIX may be prepared by reacting bis(pinacolato)diboron or bis(neopentyl glycolato)diborane respectively with a compound of formula XX or XVII as defined above; in the presence of a transition metal catalyst.

The transition metal catalyst of use in the reaction between bis(pinacolato)diboron or bis(neopentyl glycolato)diborane and compound XX or XVII is suitably dichloro[1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

The intermediates of formula XVII above may be prepared by reacting a compound of formula XXIII:

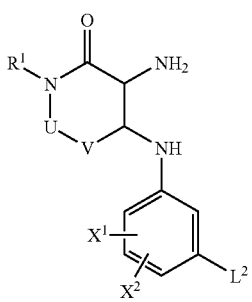

(XXIII)

wherein U, V, $X^1$, $X^2$, $R^1$ and $L^2$ are as defined above; with formic acid; under conditions analogous to those described above for the reaction between compound XIII and formic acid.

The intermediates of formula XXIII may be prepared by reaction of a compound of formula V as defined above with a compound of formula XXIV:

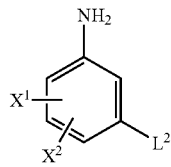

(XXIV)

wherein $X^1$, $X^2$ and $L^2$ are as defined above; under conditions analogous to those described above for the reaction between compounds XV and XVI; followed by reduction of the nitro group in the resulting compound, under conditions analogous to those described above for the reduction of the nitro group in compound XIV.

Where $L^2$ in the intermediates of formula XVII above represents triflyloxy, the relevant compound XVII may be prepared by reacting the appropriate compound of formula XXI as defined above with triflic anhydride, typically in the presence of pyridine.

The intermediates of formula XXI above may suitably be prepared from the appropriate methoxy-substituted precursor of formula XXV:

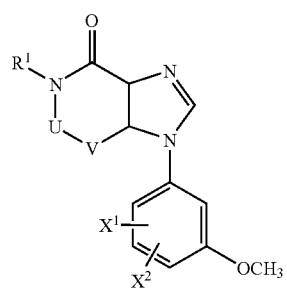

(XXV)

wherein U, V, $X^1$, $X^2$ and $R^1$ are as defined above; by treatment with boron tribromide, typically in chloroform or dichloromethane; or with hydrogen bromide, typically in acetic acid at reflux.

The intermediates of formula XXII and XXV above may be prepared by reacting a compound of formula XV as defined above with the appropriate compound of formula XXVI:

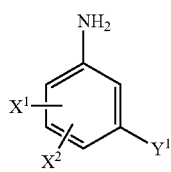

(XXVI)

wherein $X^1$ and $X^2$ are as defined above, and $Y^1$ represents amino or methoxy; under conditions analogous to those described above for the reaction between compounds XV and XVI; followed by reduction of the nitro group in the resulting compound, under conditions analogous to those described above for the reduction of the nitro group in compound XIV; followed by reaction of the product thereby obtained with formic acid, under conditions analogous to those described above for the reaction between compound XIII and formic acid.

The compounds according to the invention in which Y represents a chemical bond and Z represents pyrrol-1-yl may be prepared by reacting a compound of formula XXII as defined above with 2,5-dimethoxy-tetrahydrofuran. The reaction is conveniently accomplished at an elevated temperature in a solvent such as acetic acid.

The intermediates of formula III, IV, V, VII, VIII and IX wherein —U—V— represents —$CH_2$—$CH_2$— may be prepared from the corresponding compound wherein —U—V— represents —CH=CH— by catalytic hydrogenation.

The compounds of formula IV, VI, VIII, IX and X may conveniently be prepared by the procedures described in WO 02/10170, or by methods analogous thereto.

Where they are not commercially available, the starting materials of formula XV, XVI, XX, XXIV and XXVI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art and detailed on pages 40-42 of WO-A-02074773. A compound of formula I wherein —U—V— represents —CH=CH— may be converted into the corresponding compound wherein —U—V— represents —$CH_2$—$CH_2$— by catalytic hydrogenation.

Mixtures of products may be purified and intermediates protected as described on pages 42-43 of WO-A-02074773.

The compounds of the accompanying Examples were tested in the assay described on pages 43 and 44 of WO-A-02074773, and all were found to possess a $K_i$ value for displacement of [$^3$H]-flumazenil from the α2 and/or α3 and/or α5 subunit of the human $GABA_A$ receptor of 100 nM or less.

The following Examples illustrate the preparation of compounds according to the invention.

EXAMPLE 1

2'-Fluoro-5'-(7-methyl-8-oxo-7,8-dihydroimidazo[1,2-a]pyrazin-3-yl)-biphenyl-2-carbonitrile A suspension of 2,3-dichloropyrazine (35 g, 0.23 mol) in 25% aqueous ammonia (200 ml) was heated at 100° C. for 12 h in a PTFE-lined pressure reactor (terminal pressure 100 psi). The reaction was cooled to ambient temperature and the resulting crystalline solid collected by filtration. This solid was triturated with water (150 ml) and dried to afford 2-amino-3-chloropyrazine as a buff-coloured crystalline solid (28 g, 92%): $δ_H$ (400 MHz, DMSO) 6.78 (2H, br s), 7.56 (1H, d, J 2.5), 7.95 (1H, d, J 2.5).

Bromoacetaldehyde diethyl acetal (45 ml, 0.29 mol) was treated with water (33 ml) and 48% hydrobromic acid (33 ml) and this mixture was heated at 95° C. for 90 min. The reaction was cooled, diluted with propan-2-ol (300 ml) and treated with sodium hydrogencarbonate (33 g) added in portions. This mixture was stirred for 30 min then filtered. The filtrate was treated with 2-amino-3-chloropyrazine (25 g, 0.19 mol) and then heated at 90° C. for 16 h. The reaction was cooled to ambient temperature, concentrated to about one-third volume and then treated with 48% hydrobromic acid (25 ml). More propan-2-ol (300 ml) was added and the mixture aged for 1 h. The resulting solid was collected by filtration, washed with propan-2-ol and then dissolved in water (500 ml). This solution was made basic by adding solid sodium hydrogencarbonate and then extracted with chloroform (3×250 ml). The organics were combined, dried over anhydrous magnesium sulphate, filtered and concentrated to give a solid. Trituration with diethyl ether afforded 8-chloroimidazo[1,2-a]pyrazine as an off-white solid (18.6 g, 63%): $δ_H$ (360 MHz, DMSO) 7.73 (1H, d, J 4.5), 7.87 (1H, d, J 1), 8.28 (1H, d, J 1), 8.67 (1H, d, J 4.5).

A cooled (0° C.) suspension of 8-chloroimidazo[1,2-a]pyrazine (18.6 g, 0.12 mol) and sodium acetate (29.8 g, 0.36 mol) in methanol (125 ml, pre-saturated with solid potassium bromide) was treated with bromine (6.5 ml, 0.13 mol) added dropwise over 5 min. After stirring for 10 min thin-layer chromatography indicated no starting material. Solid sodium sulphite (15.3 g, 0.12 mol) was then added to the slurry and stirring continued for 10 min. The mixture was then treated with saturated aqueous sodium hydrogencarbonate (650 ml) added in portions. This mixture was extracted with dichloromethane (2×350 ml). The organics were combined, dried over anhydrous magnesium sulphate, filtered and concentrated to afford 3-bromo-8-chloroimidazo[1,2-a]pyrazine as a cream-coloured solid: $δ_H$ (400 MHz, $CDCl_3$) 7.82 (1H, d, J 4.5), 7.83 (1H, s), 8.05 (1H, d, J 4.6). This solid was suspended in 1:1 dichloromethane/methanol (160 ml) and treated with solid sodium methoxide (9.8 g, 0.18 mol). The resulting mixture was then stirred at 40° C. for 2 h. The reaction was cooled, diluted with water (750 ml) then extracted with dichloromethane (600 ml). The organics were dried over anhydrous magnesium sulphate, filtered and concentrated to give 3-bromo-8-methoxyimidazo[1,2-a]pyrazine as a white solid (24.5 g, 89% over 2 steps): $δ_H$ (360 MHz, DMSO) 4.06 (3H, s), 7.57 (1H, d, J 4.5), 7.81 (1H, s), 8.03 (1H, d, J 4.5).

A mixture of the above product (680 mg, 3 mmol) and 2'-fluoro-5'-(4,4,5,5-tetramethyl-[1,3,2]dioxaborolan-2-yl)-biphenyl-2-carbonitrile (prepared as described in WO 02/074773) (1.45 g, 4.5 mmol) in tetrahydrofuran (9 ml) was treated with 2M sodium carbonate (3 ml) then degassed with nitrogen for 10 min. Tetrakis(triphenylphosphine)palladium (0) (100 mg, 0.09 mmol) was added and this mixture was heated under reflux for 12 h. The reaction was cooled and the majority of the solvent removed on a rotary evaporator. The residue was partitioned between dichloromethane and water. The organics were washed with water, brine, dried over anhydrous magnesium sulphate, filtered and concentrated in vacuo. Purification of the residue by chromatography on silica gel eluting with 2% methanol in dichloromethane gave 2'-fluoro-5'-(8-methoxyimidazo[1,2-a]pyrazin-3-yl)-biphenyl-2-carbonitrile as a cream solid (768 mg, 74%): $δ_H$ (400 MHz, $CDCl_3$) 4.19 (3H, s), 7.38-7.46 (2H, m), 7.53-7.64 (4H, m), 7.71 (1H, td, J 8 and 1.5), 7.73 (1H, s), 7.85 (1H, dd, J 8 and 1), 8.02 (1H, d, J 4.5); m/z (ES$^+$) 345 [M+H]$^+$.

A suspension of the above product (750 mg, 2.2 mmol) in hydrogen bromide (30 wt % in acetic acid, 10 ml) was heated at 95° C. for 45 min. The reaction was cooled, poured into ice water and neutralised by the addition of solid sodium hydrogencarbonate. The resulting solid was collected by filtration and air-dried, then triturated with ether, to afford 2'-fluoro-5'-(8-oxo-7,8-dihydroimidazo[1,2-a]pyrazin-3-yl)biphenyl-2-carbonitrile as a cream-coloured solid (550 mg, 76%): $δ_H$ (360 MHz, DMSO) 6.92 (1H, t, J 6), 7.49 (1H, d, J 5), 7.60-7.71 (2H, m), 7.75-7.89 (5H, m), 8.03 (1H, dd, J 7 and 0.5), 11.38 (1H, d, J 5.5); m/z(ES$^+$) 331 [M+H]$^+$.

A suspension of the above product (250 mg, 0.75 mmol) in acetonitrile (10 ml) was treated with 1,1,1,3,3,3-hexamethyl-disilazane (90 μl, 0.41 mmol) and then heated at reflux for 2 h. The resulting gel-like mixture was diluted with acetonitrile (5 ml) then treated with chloro(chloromethyl)-dimethylsilane (110 μl, 0.83 mmol) and heating at reflux continued for 24 h. The reaction was cooled, the acetonitrile removed in vacuo and the residue treated with 1,2-dimethoxyethane (12 ml). Caesium fluoride (160 mg, 1.4 mmol) was then added and the reaction heated at reflux for 6 h. After cooling to ambient temperature the mixture was dissolved in 1:1 dichloromethane/methanol and pre-adsorbed onto silica. Purification by chromatography on silica eluting with 4% methanol in dichloromethane (containing 0.5% ammonia) followed by 8% methanol in dichloromethane (containing 0.5% ammonia) gave the title compound (65 mg, 25%): $\delta_H$ (400 MHz, DMSO) 3.47 (3H, s), 7.19 (1H, d, J 6), 7.57-7.88 (8H, m), 8.04 (1H, dd, J 8 and 1); m/z (ES$^+$) 345 [M+H]$^+$.

EXAMPLE 2

5'-(7-Ethyl-8-oxo-7,8-dihydroimidazo[1,2-a]pyrazin-3-yl)-2'-fluorobiphenyl-2-carbonitrile A suspension of 2'-fluoro-5'-(8-oxo-7,8-dihydroimidazo[1,2-a]pyrazin-3-yl)biphenyl-2-carbonitrile (50.0 mg, 0.51 mmol) in 1,2-dimethoxyethane (2 ml) and N,N-dimethylformamide (0.5 ml) was treated with sodium hydride (6.4 mg of a 60% dispersion in mineral oil, 0.16 mmol). After stirring at ambient temperature for 10 min, lithium bromide (26.3 mg, 0.30 mmol) was added, and stirring continued for 15 min. Iodoethane (24.2 µl, 0.30 mmol) was added and the solution heated at 65° C. for 18 h. Water (15 ml) was added and the resulting mixture was extracted with dichloromethane (3×10 ml). The combined organic layers were washed with water (10 ml), saturated sodium chloride solution (10 ml), dried over anhydrous magnesium sulphate then concentrated in vacuo. The crude product was purified by flash chromatography on silica gel, eluting with 2% methanol in dichloromethane. Crystallisation from methanol afforded the title compound as a white solid (23.9 mg, 44%): $\delta_H$ (500 MHz, CDCl$_3$) 1.38 (3H, t, J 7.2), 4.06 (2H, q, J 7.2), 6.72 (1H, d, J 5.9), 7.39 (1H, t, J 9.3), 7.44 (1H, d, J 5.9), 7.53-7.61 (5H, m), 7.69-7.73 (1H, m), 7.84 (1H, d, J 7.3); m/z (ES$^+$) 359 [M+H]$^+$.

Examples 3 and 4 are made by the method of Example 2 using 1-bromo-2-fluoroethane and 2-bromo-1,1-difluoroethane respectively.

EXAMPLE 3

2'-Fluoro-5'-[7-(2-fluoroethyl-8-oxo-7,8-dihydroimidazo[1,2-a]pyrazin-3-yl]biphenyl-2-carbonitrile $\delta_H$ (500 MHz, CDCl$_3$) 4.27 (1H, t, J 4.5), 4.32 (1H, t, J 4.5), 4.71 (1H, t, J 4.4), 4.81 (1H, t, J 4.5), 6.80 (1H, d, J 5.9), 7.40-7.43 (2H, m), 7.53-7.61 (4H, m), 7.63 (1H, s), 7.69-7.73 (1H, m), 7.85 (1H, d, J 7.7); m/z (ES$^+$) 377 [M+H]$^+$.

EXAMPLE 4

5'-[7-(2,2-Difluoroethyl)-8-oxo-7,8-dihydroimidazo[1.2-a]pyrazin-3-yl]-2'-fluorobiphenyl-2-carbonitrile $\delta_H$ (500 MHz, CDCl$_3$) 4.31 (2H, td, J 13 and 4.4), 6.14 (1H, tt, J 56 and 4.4), 6.74 (1H, d, J 6.1), 7.41 (1H, t, J 9.3), 7.46 (1H, d, J 6.1), 7.55-7.60 (4H, m), 7.65 (1H, s), 7.70-7.73 (1H, m), 7.85 (1H, d, J 7.1); m/z (ES$^+$) 395 [M+H]$^+$.

EXAMPLE 5

4,2'-Difluoro-5'-(7-methyl-8-oxo-7,8-dihydroimidazo[1,2-a]pyrazin-3-yl)-biphenyl-2-carbonitrile A suspension of 3-bromo-8-methoxyimidazo[1,2-a]pyrazine (1.6 g, 7 mmol) in hydrogen bromide (30 wt % in acetic acid, 15 ml) was heated at 80° C. for 90 min. The reaction was cooled, diluted with water (75 ml) then neutralised with solid sodium hydrogencarbonate. The resulting solid was collected by filtration, washed with water then dried under vacuum to afford 3-bromo-7H-imidazo[1,2-a]pyrazin-8-one as a white powder: $\delta_H$ (360 MHz, DMSO) 6.99 (1H, d, J 5.6), 7.29 (1H, d, J 5.6), 7.62 (1H, s). This powder was suspended in N,N-dimethylformamide (15 ml) then treated with sodium hydride (203 mg of a 60% dispersion in mineral oil, 8.4 mmol). The resulting mixture was heated at 60° C. for 20 min then treated with iodomethane (870 µl, 14 mmol). After stirring for 15 min the reaction was cooled, diluted cautiously with water (150 ml) and then extracted with dichloromethane (2×100 ml). The organics were combined, washed with water, dried over anhydrous magnesium sulphate, filtered and concentrated under high vacuum. The residue was triturated with diethyl ether and the resulting solid collected by filtration to furnish 3-bromo-7-methyl-7H-imidazo[1,2-a]pyrazin-8-one as a white solid (1.4 g, 88% over 2 steps): $\delta_H$ (360 MHz, DMSO) 3.45 (3H, s), 7.28 (1H, d, J 6), 7.39 (1H, d, J 5.6), 7.62 (1H, s).

A mixture of the above product (171 mg, 0.76 mmol), 4,2'-difluoro-5'-(5,5-dimethyl-[1,3,2]dioxaborinan-2-yl)biphenyl-2-carbonitrile (prepared as described in WO 02/074773) (392 mg, 1.2 mmol), palladium(II) acetate (7 mg, 0.03 mmol) and triphenylphosphine (8 mg, 0.03 mmol) in 1,4-dioxane (3 ml) and 2M aqueous sodium carbonate (0.75 ml) was heated at 80° C. for 3 h. The reaction was cooled then diluted with ethyl acetate (25 ml). The mixture was extracted with 4N hydrochloric acid (25 ml) and the organics discarded. The aqueous was washed with ethyl acetate, filtered through GF/A glass microfibre filter paper and the filtrate made basic with solid sodium hydrogencarbonate. The resulting solid was collected by filtration, triturated with water and dried under high vacuum to afford the title compound as a cream-coloured solid (175 mg, 64%): $\delta_H$ (600 MHz, DMSO) 3.47 (3H, s), 7.19 (1H, d, J 6.0), 7.57-7.61 (2H, m), 7.72 (1H, s), 7.76-7.86 (4H, m), 8.08 (1H, dd, J 9 and 3); m/z (ES$^+$) 363 [M+H]$^+$.

Examples 6 to 11 were made by the method of Example 5.

EXAMPLE 6

4'-Fluoro-3'-(7-methyl-8-oxo-7,8-dihydroimidazo[1,2-a]pyrazin-3-yl)-biphenyl-2-carbonitrile 4'-Fluoro-3'-(4,4,5,5-tetramethyl-[1,3,2]dioxaborolan-2-yl)biphenyl-2-carbonitrile was coupled to give the title compound as an off-white solid (40 mg, 24%): $\delta_H$ (400 MHz, d$_6$-DMSO) 3.48 (3H, s), 7.20 (1H, d, J 6), 7.43 (1H, dd, J 6 and 2), 7.61-7.66 (2H, m), 7.72-7.86 (5H, m), 8.01 (1H, dd, J 8 and 1); m/z (ES$^+$) 345 [M+H]$^+$.

EXAMPLE 7

5'-Fluoro-3'-(7-methyl-8-oxo-7,8-dihydroimidazo[1,2-a]pyrazin-3-yl)-biphenyl-2-carbonitrile 5'-Fluoro-3'-(4,4,5,5-tetramethyl-[1,3,2]dioxaborolan-2-yl)biphenyl-2-carbonitrile was coupled to give the title compound as an off-white solid (50 mg, 29%): $\delta_H$ (400 MHz, d$_6$-DMSO) 3.48 (3H, s), 7.22 (1H, d, J 6), 7.59-7.70 (5H, m), 7.79-7.87 (2H, m), 7.80 (1H, s), 8.03 (1H, dd, J 8 and 1); m/z (ES$^+$) 345 [M+H]$^+$.

EXAMPLE 8

2,2'-Difluoro-5'-(7-methyl-8-oxo-7,8-dihydroimidazo[1,2-a]pyrazin-3-yl)-biphenyl-4-carbonitrile 2,2'-Difluoro-5'-(4,4,5,5-tetramethyl-[1,3,2]dioxaborolan-2-yl)biphenyl-4-carbonitrile (prepared in the same way as in Example 19) was coupled to give the title compound as an off-white solid (30 mg, 16%): $\delta_H$ (400 MHz, $d_6$-DMSO) 3.48 (3H, a), 7.18 (1H, d, J 6), 7.59-7.61 (2H, m), 7.73 (1H, s), 7.75-7.82 (2H, m), 7.87-7.88 (2H, m), 8.05 (1H, d, J 10); m/z (ES$^+$) 363 [M+H]$^+$.

EXAMPLE 9

7-Ethyl-3-[4-fluoro-3-(2-methyl-2H-[1,2,4]triazol-3-ylmethoxy)phenyl]-7H-imidazo[1,2-a]pyrazin-8-one 3-Bromo-7-ethyl-7H-imidazo[1,2-a]pyrazin-8-one and 4-fluoro-3-(2-methyl-2H-[1,2,4]triazol-3-ylmethoxy)benzeneboronic acid were coupled to give the title compound as a white solid (43 mg, 23%): $\delta_H$ (400 MHz, $d_6$-DMSO) 1.26 (3H, t, J 7), 3.94 (3H, s), 3.96 (2H, s), 5.52 (2H, s), 7.22-7.26 (2H, m), 7.44 (1H, dd, J 11 and 8), 7.65 (1H, d, J 6), 7.64 (1H, dd, J 8 and 2), 7.66 (1H, s), 7.98 (1H, s); m/z (ES$^+$) 369 [M+H]$^+$.

EXAMPLE 10

6,2'-Difluoro-5'-(7-methyl-8-oxo-7,8-dihydroimidazo[1,2-a]pyrazin-3-yl)-biphenyl-2-carbonitrile 6,2'-Difluoro-5'-(5,5-dimethyl-[1,3,2]dioxaborinan-2-yl)biphenyl-2-carbonitrile was coupled to produce the title compound: $\delta_H$ (400 Mz, CDCl$_3$) 3.59 (3H, s), 6.71 (1H, d, J 6.0), 7.37-7.67 (8H, m); m/z (ES$^+$) 363 [M+H]$^+$.

EXAMPLE 11

4,2'-Difluoro-5'-(7-ethyl-8-oxo-7,8-dihydroimidazo[1,2-a]pyrazin-3-yl)-biphenyl-2-carbonitrile 3-Bromo-7H-imidazo[1,2-a]pyrazin-8-one (prepared as described in Example 5, 1.6 g, 7 mmol) was suspended in N,N-dimethylformamide (15 ml) then treated with sodium hydride (420 mg of a 60% dispersion in mineral oil, 10.5 mmol). The resulting mixture was heated at 60° C. for 20 min then treated with iodoethane (840 μl, 10.6 mmol). After stirring for 40 min the reaction was cooled, diluted cautiously with water (150 ml) and then extracted with dichloromethane (2×100 ml). The organics were combined, washed with water, dried over anhydrous magnesium sulphate, filtered and concentrated under high vacuum. The residue was triturated with diethyl ether and the resulting solid collected by filtration and recrystallized from ethyl acetate/methanol to furnish 3-bromo-7-ethyl-7H-imidazo[1,2-a]pyrazin-8-one as a white solid (0.34 g): $\delta_H$ (400 MHz, DMSO) 1.23 (3H, t, J 7), 3.94 (2H, q, J 7), 7.31 (1H, d, J 6), 7.41 (1H, d, J 6), 7.62 (1H, s); m/z (ES$^+$) 244 and 242 [M+H]$^+$.

Reaction of the above product under the same Suzuki coupling conditions as described in Example 5 gave the title compound after recrystallization from ethyl acetate/dichloromethane: $\delta_H$ (400 MHz, DMSO) 1.25 (3H, t, J 7.1), 3.96 (2H, q, J 7.1), 7.22 (1H, d, J 6.0), 7.57-7.61 (2H, m), 7.72 (1H, s), 7.76-7.84 (4H, m), 8.07 (1H, dd, J 8.6 and 2.7); m/z (ES$^+$) 377 [M+H]$^+$; Found C, 66.87; H, 3.54; N, 14.62. $C_{21}H_{14}F_2N_4O$ requires C, 67.02; H, 3.75; N, 14.89%.

Examples 12 to 18 were prepared in the same way as Example 10.

EXAMPLE 12

4,2'-Difluoro-5'-[7-(2,2-difluoroethyl)-8-oxo-7,8-dihydroimidazo[1,2-a]pyrazin-3-yl]biphenyl-2-carbonitrile The title compound was prepared using 2-bromo-1,1-difluoroethane: $\delta_H$ (400 MHz, DMSO) 4.44 (2H, td, J 13 and 4.4), 6.36 (1H, tt, J 56 and 4.4), 7.19 (1H, d, J 6.1), 7.60-7.65 (2H, m), 7.74-7.86 (5H, m), 8.08 (1H, dd, J 8.6 and 2.7); m/z (ES$^+$) 413 [M+H]$^+$; Found C, 60.88; H, 2.97; N, 13.38. $C_{21}H_{12}F_4N_4O$ requires C, 61.17; H, 2.93; N, 13.59%.

EXAMPLE 13

4,2'-Difluoro-5'-[7-(1-methylethyl)-8-oxo-7,8-dihydroimidazo[1,2-a]pyrazin-3-yl]biphenyl-2-carbonitrile The title compound was prepared using 2-bromopropane: 85 (400 MHz, DMSO) 1.33 (6H, d, J 6.8), 5.11 (1H, m), 7.20 (1H, d, J 6.1), 7.56-7.63 (2H, m), 7.74 (1H, m), 7.61-7.84 (4H, m), 8.06 (1H, dd, J 8.7 and 2.6); m/z (ES$^+$) 391 [M+H]+; Found C, 68.00; H, 4.04; N, 14.03. $C_{22}H_{16}F_4N_4O$ requires C, 67.79; H, 4.13; N, 14.35%.

EXAMPLE 14

4,2'-Difluoro-5'-[7-(2-fluoroethyl)-8-oxo-7,8-dihydroimidazo[1,2-a]pyrazin-3-yl]biphenyl-2-carbonitrile The title compound was prepared using 1-bromo-2-fluoroethane instead of iodoethane: $\delta_H$ (400 MHz, DMSO) 4.25 (1H, t, J 4.5), 4.31 (1H, t, J 4.5), 4.65 (1H, t, J 4.5), 4.77 (1H, t, J 4.5), 7.18 (1H, d, J 6.0), 7.59-7.62 (2H, m), 7.74 (1H, m), 7.75-7.85 (4H, m), 8.07 (1H, dd, J 8.7 and 2.6); m/z (ES$^+$) 395 [M+H]$^+$; Found C, 63.49; H, 3.27; N, 13.96. $C_{21}H_{13}F_3N_4O$ requires C, 63.96; H, 3.32; N, 14.21%.

EXAMPLE 15

4,2'-Difluoro-5'-[7-(2,2,2-trifluoroethyl)-8-oxo-7,8-dihydroimidazo[1,2-a]pyrazin-3-yl]biphenyl-2-carbonitrile The title compound was prepared using 1-iodo-2,2,2-trifluoroethane: $\delta_H$ (400 MHz, DMSO) 4.90 (2H, q, J 9.2), 7.20 (1H, d, J 6.0), 7.60-7.66 (2H, m), 7.75-7.85 (5H, m), 8.06 (1H, dd, J 8.7 and 2.6); m/z (ES$^+$) 431 [M+H]$^+$.

EXAMPLE 16

4,2'-Difluoro-5'-[7-(2-methyl-2H-[1,2,4]triazol-3-ylmethyl)-8-oxo-7,8-dihydroimidazo[1,2-a]pyrazin-3-yl]biphenyl-2-carbonitrile The title compound was prepared using 3-chloromethyl-2-methyl-2H-[1,2,4]triazole: $\delta_H$ (400 MHz, DMSO) 3.96 (3H, s), 5.35 (2H, s), 7.28 (1H, d, J 6.0), 7.62-7.64 (2H, m), 7.75-7.84 (6H, m), 8.06 (1H, dd, J 8.6 and 2.7); m/z (ES$^+$) 444 [M+H]$^+$; Found C, 62.48; H, 3.67; N, 21.98. $C_{23}H_{15}F_2N_7O$ requires C, 62.30; H, 3.41; N, 22.11%.

EXAMPLE 17

4,2'-Difluoro-5'-[8-oxo-7-(pyridin-2-ylmethyl)-7,8-dihydroimidazo[1,2-a]pyrazin-3-yl)biphenyl-2-carbonitrile The title compound was prepared using 2-chloromethylpyridine hydrochloride: $\delta_H$ (400 MHz, DMSO) 5.26 (2H, s), 7.28-7.35 (3H, m), 7.61-7.63 (2H, m), 7.76-7.86 (6H, m), 8.06 (1H, dd, J 8.6 and 2.7), 8.50 (1H, m); m/z (ES$^+$) 440 [M+H]$^+$; Found C, 68.19; H, 3.48; N, 15.69. $C_{26}H_{15}F_2N_5O$ requires C, 68.33; H, 3.44; N, 15.94%.

EXAMPLE 18

6,2'-Difluoro-5'-(7-ethyl-8-oxo-7,8-dihydroimidazo[1,2-a]pyrazin-3-yl)-biphenyl-2-carbonitrile This compound was prepared using 6,2'-difluoro-5'-(5,5-dimethyl-[1,3,2]dioxaborinan-2-yl)biphenyl-2-carbonitrile in the final step: $\delta_H$ (400 MHz, CDCl$_3$) 1.38 (3H, t, J 7.1), 4.04 (2H, q, J 7.1), 6.72 (1H, d, J 6.0), 7.38-7.67 (8H, m); m/z (ES$^+$) 377 [M+H]$^+$.

EXAMPLE 19

3-Chloro-2'-fluoro-5'-(7-methyl-8-oxo-7,8-dihydroimidazo[1,2-a]pyrazin-3-yl)biphenyl-4-carbonitrile A mixture of 4-bromo-2-chlorobenzonitrile (2.2 g, 10 mmol) and 2-fluorobenzeneboronic acid (1.82 g, 13 mmol) in tetrahydrofuran (30 ml) was treated with 2M sodium carbonate (13 ml) then degassed with nitrogen for 10 min. Tetrakis(triphenylphosphine)palladium(0) (0.58 g, 0.5 mmol) was added and this mixture was heated under reflux for 12 h. The resulting mixture was partitioned between dichloromethane and water. The organics were washed with water, brine, dried over anhydrous magnesium sulphate, filtered and concentrated in vacuo. Purification of the residue by chromatography on silica gel eluting with isohexane on a gradient of ethyl acetate (5-15%) gave 3-chloro-2'-fluorobiphenyl-4-carbonitrile as a white solid (2.3 g, 99%): $\delta_H$ (400 MHz, CDCl$_3$) 7.17-7.57 (5H, m), 7.64-7.75 (2H, m).

To a slurry of the above product (2.3 g, 10 mmol) and 1,3-dibromo-5,5-dimethylhydantoin (3.1 g, 11 mmol) in acetonitrile (20 ml) was added concentrated sulphuric acid (0.8 ml). The slurry was warmed to 70° C. and the resulting solution stirred at 70° C. for 16 h. After 16 h, the reaction was complete. Water (75 ml) was added and the resulting suspension was filtered and dried, to give 5'-bromo-3-chloro-2'-fluorobiphenyl-4-carbonitrile as an off-white solid (3.1 g, 98%): $\delta_H$ (360 MHz, CDCl$_3$) 7.07-7.17 (1H, m), 7.29-7.76 (5H, m).

The above product (0.6 g, 2 mmol), 4,4,5,5,4',4',5',5'-octamethyl-[2,2']bi{[1,3,2]dioxaborolanyl} (0.6 g, 2.4 mmol) and potassium acetate (0.39 g, 4 mmol) were suspended in 1,4-dioxane (6 ml) and the mixture was degassed with nitrogen for 10 minutes, before adding 1,1'-bis(diphenylphosphino)ferrocene-dichloropalladium(II) complex with dichloromethane (0.05 g, 0.06 mmol). The resulting mixture was heated at 90° C. for 12 h. The mixture was cooled to ambient temperature, filtered and the filter-cake washed with dichloromethane. The filtrate was evaporated to dryness and the residue stirred with ice-cold 2N sodium hydroxide (70 ml) for 20 minutes. The aqueous mixture was filtered and the filtrate washed with diethyl ether (2×50 ml). The organics were discarded and the aqueous phase cooled to 0° C. before lowering the pH to 6 by addition of 36% hydrochloric acid. The product was extracted into diethyl ether to give 3-chloro-2'-fluoro-5'-(4,4,5,5-tetramethyl-[1,3,2]dioxaborolan-2-yl)biphenyl-4-carbonitrile as a yellow oil (0.53 g, 74%).

3-Bromo-7-methyl-7H-imidazo[1,2-a]pyrazin-8-one and the above product were coupled in the same way as in Example 5 to give the title compound as an off-white solid (50 mg, 26%): $\delta_H$ (360 MHz, d$_6$-DMSO) 3.48 (3H, s), 7.18 (1H, d, J 6), 7.56-7.59 (2H, m), 7.70-7.90 (2H, m), 8.12 (2H, dd, J 8 and 3); m/z (ES$^+$) 379 [M+H]$^+$.

EXAMPLE 20

3-[4-Fluoro-3-(1-methyl-1H-[1,2,3]triazol-4-ylmethoxy)phenyl]-7-methyl-7H-imidazo[1,2-a]pyrazin-8-one A cooled (−20° C.) solution of 2,2,6,6-tetramethylpiperidine (28 ml, 165 mmol) in tetrahydrofuran (400 ml) was treated with n-butyllithium (63 ml of a 2.5M solution in hexanes, 157.5 mmol). This mixture was then cooled to −78° C. 1-Bromo-4-fluorobenzene (16.5 ml, 150 mmol) was then added neat and dropwise over 10 min and stirring at −78° C. was continued for 3 h. Triisopropyl borate (40 ml, 172.5 mmol) was then added and stirring at −78° C. continued for 30 min before removing the cooling bath. When the internal temperature of the reaction reached −40° C., 5N hydrochloric acid was added (75 ml) and the mixture was stirred to ambient temperature. After stirring at ambient temp for 1 h the majority of the tetrahydrofuran was removed and the mixture partitioned between ether (500 ml) and 1N hydrochloric acid (500 ml). The organics were then extracted with 2N sodium hydroxide (400 ml) and the organics were discarded. The aqueous was cooled in an ice-water bath and 5N hydrochloric acid (150 ml) was added dropwise over 15 min. The resulting white solid was collected and dried under vacuum to afford 5-bromo-2-fluorobenzeneboronic acid (25 g, 76%).

A solution of the above product (25 g, 114 mmol) in tetrahydrofuran was treated with hydrogen peroxide (7.8 ml of a 35 wt % solution in water) then with sodium hydroxide (1.4 ml of a 4N solution in water). A mild exotherm caused the internal temperature to reach 40° C. This mixture was left to stir at ambient temperature for 14 h then treated with manganese dioxide (200 mg) and stirring was continued for 90 min before filtering the reaction (GF/A filter paper). The filtrate was concentrated on a rotary evaporator and the residue partitioned between ether (400 ml) and water. The organics were washed with more water, brine and dried over anhydrous magnesium sulphate. Filtration and evaporation to dryness afforded 5-bromo-2-fluorophenol (19.7 g, 90%) as a colourless liquid: $\delta_H$ (400 MHz, d$_6$-DMSO) 6.93-6.97 (1H, m), 7.09-7.14 (2H, m), 10.36 (1H, br).

An ice-cooled solution of the above product (1.91 g, 10 mmol), (1-methyl-1H-[1,2,3]triazol-4-yl)methanol (1.24 g, 11 mmol) and triphenylphosphine (3.93 g, 15 mmol) in tetrahydrofuran (50 ml) was treated dropwise with diisopropyl azodicarboxylate (3.03 g, 15 mmol) over 10 min. The resulting mixture was stirred to ambient temperature over 12 h and then glacial acetic acid (1 ml) was added. The reaction mixture was concentrated in vacuo then partitioned between ethyl acetate and 0.01N sodium hydroxide solution. The organics were washed with water, brine, dried over anhydrous magnesium sulphate and concentrated to give an oil. This oil was purified by chromatography on silica gel eluting with isohexane on a gradient of ethyl acetate (20-50%). Product-containing fractions were concentrated and the resulting residue triturated with 10% ether in isohexane to furnish 4-(5-bromo-2-fluorophenoxymethyl)-1-methyl-1H-[1,2,3]triazole as a white solid (1.9 g, 66%): $\delta_H$ (360 MHz, $d_6$-DMSO) 4.06 (3H, s), 5.25 (2H, s), 7.10-7.20 (2H, m), 7.55-7.70 (1H, m), 8.19 (1H, s).

The above product was converted to 4-fluoro-3-(1-methyl-1H-[1,2,3]triazol-4-ylmethoxy)-benzeneboronic acid as described in Example 19: $\delta_H$ (400 MHz, $d_6$-DMSO) 4.06 (3H, s), 5.19 (2H, s), 7.16 (1H, dd, J 12 and 8), 7.38-7.41 (1H, m), 7.71 (1H, dd, J 9 and 1), 8.09 (2H, s), 8.16 (1H, s).

The above product was coupled as described in Example 5 to afford the title compound as a white solid: $\delta_H$ (400 MHz, $d_6$-DMSO) 3.48 (3H, s), 4.06 (3H, s), 5.35 (2H, s), 7.17-7.21 (2H, m), 7.39 (1H, dd, J 11 and 8), 7.55 (1H, d, J 6), 7.60 (1H, dd, J 8 and 2), 7.67 (1H, s), 8.22 (1H, s); m/z (ES$^+$) 355 [M+H]$^+$.

EXAMPLE 21

3-[4-Fluoro-3-(2-methyl-2H-[1,2,4]triazol-3-yl-methoxy)phenyl]-7-methyl-7H-imidazo[1,2-a]pyrazin-8-one A cooled (0° C.) solution of 5-bromo-2-fluorophenol, (2-methyl-2H-[1,2,4]triazol-3-yl)methanol and triphenylphosphine in tetrahydrofuran was treated dropwise with diisopropyl azodicarboxylate over 10 min. The resulting mixture was stirred overnight and then acetic acid was added. The reaction mixture was evaporated to dryness and the residue was partitioned between ethyl acetate and 0.01N sodium hydroxide solution. The organic phase was washed with water and brine, dried over anhydrous magnesium sulphate and pre-adsorbed onto silica. Purification by flash column chromatography on silica gel, eluting with isohexane on a gradient of ethyl acetate (10-50%), led to product-containing fractions that were combined. The material was further purified by flash column chromatography on silica gel, eluting with dichloromethane containing 1% ammonia on a gradient of methanol (0.5-3%), to give 5-(5-bromo-2-fluoro-phenoxymethyl)-1-methyl-1H-[1,2,4]triazole as an off-white solid (2.1 g, 37%): $\delta_H$ (360 MHz, CDCl$_3$) 4.01 (3H, s), 5.29 (2H, s), 6.96-6.99 (1H, m), 7.09-7.13 (1H, m), 7.29 (1H, dd, J 5 and 2), 7.88 (1H, s); m/z (ES$^+$) 288 [MH$^+$].

The above product was reacted with 4,4,5,5,4',4',5',5'-octamethyl-[2,2']bi{[1,3,2]-dioxaborolanyl} as described in Example 19 to give the title compound as a pale yellow solid (0.43 g, 62%).

The above product was coupled in the same way as in Example 5 to give the title compound as a white solid (58 mg, 33%): $\delta_H$ (400 MHz, $d_6$-DMSO) 3.48 (3H, s), 3.94 (3H, s), 5.52 (2H, s), 7.21-7.25 (2H, m), 7.45 (1H, dd, J 11 and 8), 7.53 (1H, d, J 6), 7.62 (1H, dd, J 8 and 2), 7.65 (1H, s), 7.98 (1H, s); m/z (ES$^+$) 355 [M+H]$^+$.

EXAMPLE 22

4,2'-Difluoro-5'-(7-methyl-8-oxo-5,6,7,8-tetrahydroimidazo[1,2-a]pyrazin-3-yl)biphenyl-2-carbonitrile A suspension of 8-chloroimidazo[1,2-a]pyrazine (5 g, 325 mmol) in 5N hydrochloric acid (35 ml) was heated at 90° C. for 14 h. The reaction mixture was cooled, then concentrated using rotary evaporation. Azeotropic removal of water with toluene (2×30 ml) gave 8-oxo-7,8-dihydroimidazo[1,2-a]pyrazine hydrochloride (5.7 g): $\delta_H$ (360 MHz, DMSO) 7.01 (1H, d, J 5.6), 7.60 (1H, d, J 5.6), 7.70 (1H, s), 7.97 (1H, s), 11.59 (1H, br s).

The above product (1 g) was suspended in N,N-dimethylformamide (15 ml) then treated with sodium hydride (650 mg of a 60% dispersion in mineral oil). The resulting mixture was heated at 60° C. for 20 min then cooled to room temperature and treated with iodomethane (0.4 ml). After stirring for 15 h the reaction mixture was diluted cautiously with methanol (5 ml) and then silica gel (5 g) was added and the solvents removed under vacuum. The silica residue was filtered through a plug of silica gel, using 10% methanol in dichloromethane as eluent, then the solvents were removed in vacuo to leave 7-methyl-7H-imidazo[1,2-a]pyrazin-8-one (1.15 g): $\delta_H$ (360 MHz, DMSO) 3.43 (3H, s), 7.11 (1H, d, J 5.8), 7.46 (1H, s), 7.56 (1H, d, J 5.8), 7.78 (1H, s). NOE studies showed that irradiation of the 3H singlet at δ 3.43 gave enhancement of the doublet at δ 7.11 and vice-versa indicating that methylation took place on the 7-nitrogen rather than the 8-oxygen.

The above product (315 mg, 2.1 mmol) in a Parr flask was dissolved in methanol (20 ml) and 10% Pd—C catalyst (100 mg) was added. The reaction mixture was shaken under 55 psi of hydrogen for 16 days then filtered and concentrated under vacuum to leave a residue. This was recrystallized from ethyl acetate/methanol to give 7-methyl-8-oxo-5,6,7,8-tetrahydroimidazo[1,2-a]pyrazine (185 mg): $\delta_H$ (360 MHz, DMSO) 3.31 (3H, s), 3.70-3.73 (2H, m), 4.24-4.28 (2H, m), 7.08 (1H, s), 7.32 (1H, s).

The above product (80 mg, 0.53 mmol) and 5'-bromo-4,2'-difluorobiphenyl-2-carbonitrile (prepared as described in WO 02/074773, 204 mg, 1.3 mol eq) were dissolved in DMA (2 ml) and potassium acetate (280 mg, 1.5 mol eq), palladium acetate (6 mg, 5 mol %) and triphenylphosphine (7 mg, 5 mol %) were all added. After bubbling nitrogen through the reaction mixture for 10 min, the temperature was raised to 130° C. and heating continued for 3 h. After cooling, the crude reaction mixture was poured onto a column of silica and purified using 0-5% methanol in dichloromethane as eluent. Recrystallization from ethyl acetate/dichloromethane gave the title compound (18 mg), mp 224° C.: $\delta_H$ (400 MHz, DMSO) 3.02 (3H, s), 3.72-3.75 (2H, m), 4.35-4.38 (2H, m), 7.38 (1H, s), 7.57 (1H, m), 7.72-7.78 (4H, m), 8.06 (1H, dd, J 9 and 3); m/z (ES$^+$) 365 [M+H]$^+$.

Examples 23 and 24 were prepared by the method of Example 22:

EXAMPLE 23

5,2'-Difluoro-5'-(7-methyl-8-oxo-5,6,7,8-tetrahydroimidazo[1,2-a]pyrazin-3-yl)biphenyl-2-carbonitrile The title compound was prepared using 5'-bromo-5,2'-difuorobiphenyl-2-carbonitrile in the final step: $\delta_H$ (400 MHz, CDCl$_3$) 3.18 (3H, s), 3.75-3.77 (2H, m), 4.32-4.34 (2H, m), 7.24-7.28 (1H, m), 7.30-7.38 (3H, m), 7.44-7.46 (1H, m), 7.52-7.55 (1H, m), 7.83 (1H, dd, J 7 and 4); m/z (ES$^+$) 365 [M+H]$^+$.

EXAMPLE 24

6,2'-Difluoro-5'-(7-methyl-8-oxo-5,6,7,8-tetrahydroimidazo[1,2-a]pyrazin-3-yl)biphenyl-2-carbonitrile The title compound was prepared using 5'-bromo-6,2'-difluorobiphenyl-2-carbonitrile in the final step: $\delta_H$ (400 MHz, CDCl$_3$) 3.19 (3H, s), 3.73-3.78 (2H, m), 4.28-4.35 (2H, m), 7.34-7.42 (3H, m), 7.45-7.49 (1H, m), 7.54-7.58 (2H, m), 7.64 (1H, m); m/z (ES$^+$) 365 [M+H]$^+$.

EXAMPLE 25

4,2'-Difluoro-5'-(7-ethyl-8-oxo-5,6,7,8-tetrahydroimidazo[1,2-a]pyrazin-3-yl)biphenyl-2-carbonitrile 8-Oxo-7,8-dihydroimidazo[1,2-a]pyrazine hydrochloride (see Example 20, 1 g) in a Parr flask was dissolved in methanol (60 ml) and 10% Pd—C catalyst (300 mg) was added. The reaction mixture was shaken under 55 psi of hydrogen for 17 days then filtered and concentrated under vacuum to leave a residue. This was recrystallized from ethyl acetate/methanol to give 8-oxo-5,6,7,8-tetrahydroimidazo[1,2-a]pyrazine hydrochloride (610 mg): $\delta_H$ (360 MHz, DMSO) 3.66-3.70 (2H, m), 4.36-4.39 (2H, m), 7.67 (1H, s), 7.78 (1H, s), 8.84 (1H, br s).

The above product (500 mg, 40 mmol) was suspended in N,N-dimethylformamide (10 ml) then treated with sodium hydride (380 mg of a 60% dispersion in mineral oil, 2.4 mol eq). The resulting mixture was heated at 60° C. for 20 min then cooled to room temperature and treated with iodoethane (0.386 ml, 1.2 mol eq). After stirring for 15 h the reaction mixture was diluted cautiously with methanol (5 ml) and then silica gel (4 g) was added and the solvents removed under vacuum. The silica residue was filtered through a plug of silica gel, using 10% methanol in dichloromethane as eluent, then the solvents were removed in vacuo to leave 7-ethyl-8-oxo-5,6,7,8-tetrahydroimidazo[1,2-a]pyrazine (400 mg): $\delta_H$ (400 MHz, DMSO) 1.10 (3H, t, J 7.2), 3.47 (2H, J 7.2), 3.70-3.73 (2H, m), 4.23-4.27 (2H, m), 7.08 (1H, s), 7.32 (1H, s).

The above product (82.5 mg, 0.53 mmol) and 5'-bromo-4,2'-difluorobiphenyl-2-carbonitrile (prepared as described in WO 02/074773, 204 mg, 1.3 mol eq) were dissolved in DMA (2 ml) and potassium acetate (280 mg, 1.5 mol eq), palladium acetate (6 mg, 5 mol %) and triphenylphosphine (7 mg, 5 mol %) were all added. After bubbling nitrogen through the reaction mixture for 10 min, the temperature was raised to 130° C. and heating continued for 3 h. After cooling, the crude reaction mixture was poured onto a column of silica and purified using 0-5% methanol in dichloromethane as eluent. Recrystallation from ethyl acetate/dichloromethane gave the title compound (18 mg): $\delta_H$ (400 MHz, DMSO) 1.12 (3H, t, J 7.1), 3.51 (2H, q, J 7.1), 3.73-3.76 (2H, m), 4.34-4.37 (2H, m), 7.39 (1H, s), 7.57 (1H, m), 7.72-7.78 (4H, m), 8.06 (1H, dd, J 9 and 3); m/z (ES$^+$) 379 [M+H]$^+$.

Examples 26 to 28 were prepared using the method of Example 25 using 5'-bromo-5,2'-difluorobiphenyl-2-carbonitrile and 5'-bromo-6,2'-difluorobiphenyl-2-carbonitrile respectively (prepared as described in WO 02/074773):

EXAMPLE 26

5,2'-Difluoro-5'-(7-ethyl-8-oxo-5,6,7,8-tetrahydroimidazo[1,2-a]pyrazin-3-yl)biphenyl-2-carbonitrile This compound was prepared using 5'-bromo-5,2'-difluorobiphenyl-2-carbonitrile (prepared as described in WO 02/074773): $\delta_H$ (400 MHz, DMSO) 1.11 (3H, t, J 7.1), 3.51 (2H, q, J 7.1), 3.73-3.76 (2H, m), 4.35-4.38 (2H, m), 7.40 (1H, s), 7.55-7.61 (2H, m), 7.68-7.78 (3H, m), 8.13 (1H, dd, J 9 and 3); m/z (ES$^+$) 379 [M+H]$^+$.

EXAMPLE 27

6,2'-Difluoro-5'-(7-ethyl-8-oxo-5,6,7,8-tetrahydroimidazo[1,2-a]pyrazin-3-yl)biphenyl-2-carbonitrile $\delta_H$ (400 MHz, DMSO) 1.20 (3H, t, J 7.1), 3.59 (2H, q, J 7.1), 3.82-3.85 (2H, m), 4.39-4.45 (2H, m), 7.45 (1H, s), 7.65-7.70 (1H, m), 7.83-7.92 (4H, m), 8.00 (1H, dd, J 9 and 3); m/z (ES$^+$) 379 [M+H]$^+$.

EXAMPLE 28

4,2'-Difluoro-5'-[8-oxo-7-(pyridin-2-ylmethyl)-5,6,7,8-tetrahydro-imidazo[1,2-a]pyrazin-3-yl)biphenyl-2-carbonitrile 8-Oxo-5,6,7,8-tetrahydroimidazo[1,2-a]pyrazine hydrochloride (87 mg, 0.53 mmol), prepared as described in Example 25, was reacted with 5'-bromo-4,2'-difluorobiphenyl-2-carbonitrile (prepared as described in WO 02/074773, 204 mg, 1.3 mol eq) in DMA (2 ml) in the presence of potassium acetate (280 mg, 1.5 mol eq), palladium acetate (6 mg, 5 mol %) and triphenylphosphine (7 mg, 5 mol %). After bubbling nitrogen through the reaction mixture for 10 min, the temperature was raised to 130° C. and heating continued for 3 h. After cooling, the crude reaction mixture was poured onto a column of silica and purified using 0-5% methanol in dichloromethane as eluent. Recrystallization from ethyl acetate/dichloromethane gave 4,2'-difluoro-5'-(8-oxo-7,8-dihydroimidazo[1,2-a]pyrazin-3-yl)biphenyl-2-carbonitrile (126 mg): $\delta_H$ (400 MHz, DMSO) 3.54-3.58 (2H, m), 4.28-4.32 (2H, m), 7.39 (1H, s), 7.54-7.59 (1H, m), 7.71-7.78 (4H, m), 8.05-8.08 (1H, m), 8.18 (1H, br s); m/z (ES$^+$) 351 [M+H]$^+$.

The title compound was prepared using the method described in the first part of Example 11, using 2-chloromethylpyridine hydrochloride: $\delta_H$ (400 MHz, DMSO) 3.60-3.64 (2H, m), 4.18-4.22 (2H, m), 4.60 (2H, m), 7.08-7.11 (1H, m), 7.16-7.19 (1H, m), 7.21 (1H, s), 7.54-7.59 (1H, m), 7.52-7.56 (5H, m), 7.82-7.86 (1H, m), 8.30-8.32 (1H, m); m/z (ES$^+$) 442 [M+H]$^+$.

EXAMPLE 29

4,2'-Difluoro-5'-(7-methyl-8-oxo-7,8-dihydroimidazo[1,2-d][1,2,4]triazin-3-yl)biphenyl-2-carbonitrile 2-Hydrazinocarbonylimidazole (prepared according to the procedure described in EP-A-0713876) (1.00 g, 7.93 mmol) was suspended in Dowtherm A (6 ml), N,N-dimethylformamide dimethyl acetal (1.89 g, 15.9 mmol) added and the mixture heated at 100° C. for 1.5 h then at 210° C. for 18 h. The mixture was allowed to cool to room temperature, diethyl ether (100 ml) added and the precipitated solid was filtered. The brown solid was purified by dry flash column chromatography on silica eluting with dichloromethane (+0.1% 0.880 ammonia) on a gradient of methanol (5-12%). Collecting appropriate fractions gave 7H-imidazo[1,2-d][1,2,4]triazin-8-one (216 mg, 20%) as an off-white solid: $\delta_H$ (400 MHz, CDCl$_3$) 7.59 (1H, d, J 1), 7.91 (1H, d, J 1), 8.74 (1H, s), 12.39 (1H, s).

Sodium hydride (60% suspension in mineral oil) (76 mg, 1.90 mmol) was added to a suspension of the above product (216 mg, 1.59 mmol) in N,N-dimethylformamide (4 ml) and the mixture stirred at 20° C. for 10 min then at 60° C. for 5 min. The mixture was allowed to cool to ambient temperature, methyl iodide (676 mg, 4.76 mmol) added and the mixture left to stir for 10 min. The solvent was evaporated and the residue was purified by flash column chromatography on silica eluting with dichloromethane on a gradient of methanol (2-4%). Collecting appropriate fractions gave 7-methyl-7H-imidazo[1,2-d][1,2,4]triazin-8-one (150 mg, 63%) as a pale yellow solid: $\delta_H$ (360 MHz, CDCl$_3$) 7.45 (1H, d, J 1), 7.63 (1H, d, J 1), 8.19 (1H, s).

The above product (75 mg, 0.50 mmol), 5'-bromo-4,2'-difluorobiphenyl-2-carbonitrile (prepared according to the procedure described in WO 02/38568) (220 mg, 0.75 mmol) and potassium acetate (74 mg, 0.75 Mmol) were suspended in N,N-dimethylacetamide (2 ml) and degassed with nitrogen for 10 min. Palladium(II) acetate (5.6 mg, 0.025 mmol) and triphenylphosphine (6.6 mg, 0.025 mmol) were added and the mixture heated at 130° C. for 2 h. The mixture was allowed to cool to ambient temperature, diluted with ethyl acetate (100 ml) and washed with water (50 ml) and brine (50 ml), dried over anhydrous sodium sulfate, filtered and evaporated to give a yellow solid. The solid was purified by flash column chromatography on silica eluting with 2% methanol in dichloromethane. Collecting appropriate fractions followed by trituration with diethyl ether gave the title compound as a white solid: $\delta_H$ (400 MHz, CDCl$_3$) 3.80 (3H, s), 7.41-7.47 (2H, m), 7.53-7.64 (4H, m), 7.67 (1H, s), 8.42 (1H, s); m/z (ES$^+$) 364 (M$^+$+H).

EXAMPLE 30

3'-(1-Methyl-6-oxo-1,6-dihydropurin-9-yl)biphenyl-2-carbonitrile

Sodium methoxide (2.70 g, 50.0 mmol) was added portionwise over 10 min to a 0° C. suspension of 4,6-dichloro-5-nitropyrimidine (4.85 g, 25.0 mmol) in methanol (90 ml). On complete addition the mixture was stirred at 0° C for 2 h. The precipitate was filtered and the filtrate evaporated. The residue was suspended in isohexane and filtered. The filtrate was evaporated and the residue purified by flash column chromatography on silica, eluting with 5% ethyl acetate in isohexane. Collecting appropriate fractions gave 4-chloro-6-methoxy-5-nitropyrimidine (3.50 g, 74%) as a white solid: $\delta_H$ (400 MHz, CDCl$_3$) 4.15 (3H, s), 8.65 (1H, s).

The above product (3.50 g, 18.5 mmol) and 3'-aminobiphenyl-2-carbonitrile (prepared according to the procedure described in WO 02/38568) (3.23 g, 16.6 mmol) were dissolved in triethylamine (9.32 g, 92.3 mmol) and dimethylsulfoxide (10 ml) and heated at 90° C. for 18 h. The mixture was allowed to cool to ambient temperature then poured onto water (150 ml) and extracted with ethyl acetate (2×300 ml). The organic fractions were combined, washed with water (3×75 ml) and brine (50 ml), dried over anhydrous sodium sulfate, filtered and evaporated to give a brown solid. The brown solid was triturated with diethyl ether (50 ml), filtered, washed with diethyl ether (2×10 ml) and left to air dry, which gave 3'-(1-methyl-5-nitro-6-oxo-1,6-dihydropyrimidin-4-ylamino)biphenyl-2-carbonitrile (2.24 g, 38%) as a yellow solid: $\delta_H$ (360 MHz, CDCl$_3$) 3.52 (3H, s), 7.45-7.57 (5H, m), 7.68 (1H, ddd, J 8, 8 and 1), 7.78-7.82 (2H, m), 8.04 (1H, s), 11.13 (1H, s).

The above product (100 mg, 0.28 mmol) was suspended in THF (5 ml) and ethanol (5 ml), tin(II) chloride (162 mg, 0.72 mmol) added and the mixture heated under reflux for 18 h. The solvent was evaporated and the residue suspended in formic acid (20 ml) and heated under reflux for 48 h. The mixture was allowed to cool to ambient temperature and the solvent evaporated. The residue was dissolved in dichloromethane and methanol and evaporated onto silica. The product was purified by flash column chromatography on the same, eluting with dichloromethane (+0.1% 0.880 ammonia) on a gradient of methanol (2-5%). Collecting appropriate fractions gave the title compound (35 mg, 37%) as a white solid: $\delta_H$ (500 MHz, DMSO) 3.55 (3H, s), 7.65 (1H, dd, J 8 and 8), 7.72-7.79 (3H, m), 7.85 (1H, ddd, J 8, 8 and 1), 7.97 (1H, dd, J 8 and 1), 8.00-8.04 (2H, m), 8.45 (1H, s), 8.59 (1H, s); m/z (ES$^+$) 328 (M$^+$+H).

The invention claimed is:
1. A compound of the formula I:

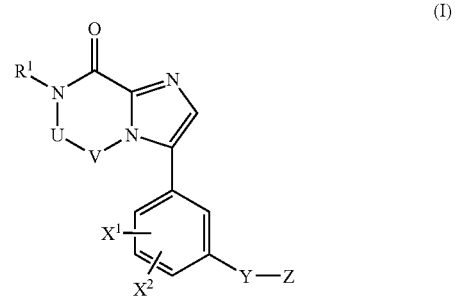

wherein:
—U—V— represents —CH=CH—, or —CH$_2$—CH$_2$—;
X$^1$ represents hydrogen, halogen, C$_{1-6}$ alkyl, trifluoromethyl or C$_{1-6}$ alkoxy;
X$^2$ represents hydrogen or halogen;
Y represents a chemical bond;
Z represents a substituted phenyl or triazolyl group, wherein the substituent is selected from fluoro, chloro, cyano, nitro, methyl, hydroxy, methoxy, oxy, methanesulphonyl, amino, aminocarbonyl, formyl, methoxycarbonyl and —CH=NOH;
R$^1$ represents C$_{1-6}$ alkyl, halo(C$_{1-6}$)alkyl, methyl-triazolylmethyl or pyridinylmethyl;
or a pharmaceutically acceptable salt thereof.

2. The compound of claim 1 wherein —U—V— represents —CH=CH—.

3. The compound of claim 1 wherein R$^1$ is methyl, ethyl, fluoroethyl, difluoroethyl, trifluoroethyl, isopropyl, methyl-triazolylmethyl or pyridinylmethyl.

4. The compound of claim 1 wherein X$^1$ is fluorine and X$^2$ is hydrogen.

5. The compound of claim 1 wherein Z is a substituted phenyl or triazolyl group, wherein the substituent is selected from fluoro, chloro, cyano and methyl.

6. A compound of claim 1, which is selected from the group consisting of:
2'-fluoro-5'-(7-methyl-8-oxo-7,8-dihydroimidazo[1,2-a]pyrazin-3-yl)-biphenyl-2-carbonitrile;
5'-(7-ethyl-8-oxo-7,8-dihydroimidazo[1,2-a]pyrazin-3-yl)-2'-fluorobiphenyl-2-carbonitrile;
2'-fluoro-5'-[7-(2-fluoroethyl)-8-oxo-7,8-dihydroimidazo[1,2-a]pyrazin-3-yl]biphenyl-2-carbonitrile;
5'-[7-(2,2-difluoroethyl)-8-oxo-7,8-dihydroimidazo[1,2-a]pyrazin-3-yl]-2'-fluorobiphenyl-2-carbonitrile;
4,2'-difluoro-5'-(7-methyl-8-oxo-7,8-dihydroimidazo[1,2-a]pyrazin-3-yl)-biphenyl-2-carbonitrile;
4,2'-difluoro-5'-(7-ethyl-8-oxo-7,8-dihydroimidazo[1,2-a]pyrazin-3-yl)-biphenyl-2-carbonitrile;

4,2'-difluoro-5'-[7-(2,2-difluoroethyl)-8-oxo-7,8-dihydroimidazo[1,2-a]pyrazin-3-yl]biphenyl-2-carbonitrile;

4,2'-difluoro-5'-[7-(1-methylethyl)-8-oxo-7,8-dihydroimidazo[1,2-a]pyrazin-3-yl]biphenyl-2-carbonitrile;

3-chloro-2'-fluoro-5'-(7-methyl-8-oxo-7,8-dihydroimidazo[1,2-a]pyrazin-3-yl)biphenyl-4-carbonitrile;

4,2'-difluoro-5'-[7-(2-fluoroethyl)-8-oxo-7,8-dihydroimidazo[1,2-a]pyrazin-3-yl]biphenyl-2-carbonitrile;

4'-fluoro-3'-(7-methyl-8-oxo-7,8-dihydroimidazo[1,2-a]pyrazin-3-yl)-biphenyl-2-carbonitrile;

5'-fluoro-3'-(7-methyl-8-oxo-7,8-dihydroimidazo[1,2-a]pyrazin-3-yl)-biphenyl-2-carbonitrile;

2,2'-difluoro-5'-(7-methyl-8-oxo-7,8-dihydroimidazo[1,2-a]pyrazin-3-yl)-biphenyl-4-carbonitrile;

4,2'-difluoro-5'-[7-(2,2,2-trifluoroethyl)-8-oxo-7,8-dihydroimidazo[1,2-a]pyrazin-3-yl]biphenyl-2-carbonitrile;

4,2'-difluoro-5'-[7-(2-methyl-2H-[1,2,4]triazol-3-ylmethyl)-8-oxo-7,8-dihydroimidazo[1,2-a]pyrazin-3-yll-biphenyl-2-carbonitrile;

3-[4-fluoro-3-(1-methyl-1H-[1,2,3]triazol-4-ylmethoxy)phenyl]-7-methyl-7H-imidazo[1,2-a]pyrazin-8-one;

3-[4-fluoro-3-(2-methyl-2H-[1,2,4]triazol-3-ylmethoxy)phenyl]-7-methyl-7H-imidazo[1,2-a]pyrazin-8-one;

7-ethyl-3-[4-fluoro-3-(2-methyl-2H-[1,2,4]triazol-3-ylmethoxy)phenyl]-7H-imidazo[1,2-a]pyrazin-8-one;

4,2'-difluoro-5'-[8-oxo-7-(pyridin-2-ylmethyl)-7,8-dihydroimidazo[1,2-a]pyrazin-3-yl)biphenyl-2-carbonitrile;

4,2'-difluoro-5'-(7-methyl-8-oxo-5,6,7,8-tetrahydroimidazo[1,2-a]pyrazin-3-yl)biphenyl-2-carbonitrile;

4,2'-difluoro-5'-(7-ethyl-8-oxo-5,6,7,8-tetrahydroimidazo[1,2-a]pyrazin-3-yl)biphenyl-2-carbonitrile;

5,2'-difluoro-5'-(7-ethyl-8-oxo-5,6,7,8-tetrahydroimidazo[1,2-a]pyrazin-3-yl)biphenyl-2-carbonitrile;

6,2'-difluoro-5'-(7-ethyl-8-oxo-5,6,7,8-tetrahydroimidazo[1,2-a]pyrazin-3-yl)biphenyl-2-carbonitrile;

6,2'-difluoro-5'-(7-methyl-8-oxo-7,8-dihydroimidazo[1,2-a]pyrazin-3-yl)-biphenyl-2-carbonitrile;

6,2'-difluoro-5'-(7-ethyl-8-oxo-7,8-dihydroimidazo[1,2-a]pyrazin-3-yl)-biphenyl-2-carbonitrile;

5,2'-difluoro-5'-(7-methyl-8-oxo-5,6,7,8-tetrahydroimidazo[1,2-a]pyrazin-3-yl)biphenyl-2-carbonitrile;

4,2'-difluoro-5'-[8-oxo-7-(pyridin-2-ylmethyl)-5,6,7,8-tetrahydro-imidazo[1,2-a]pyrazin-3-yl)biphenyl-2-carbonitrile;

6,2'-difluoro-5'-(7-methyl-8-oxo-5,6,7,8-tetrahydroimidazo[1,2-a]pyrazin-3-yl)biphenyl-2-carbonitrile;

or a pharmaceutically acceptable salt thereof.

7. A pharmaceutical composition comprising the compound of claim 1 or a pharmaceutically acceptable salt thereof, and a pharmaceutically acceptable exicipient.

8. A pharmaceutical composition comprising the compound of claim 6 or a pharmaceutically acceptable salt thereof, and a pharmaceutically acceptable exicipient.

* * * * *

UNITED STATES PATENT AND TRADEMARK OFFICE
CERTIFICATE OF CORRECTION

PATENT NO. : 7,485,640 B2  Page 1 of 1
APPLICATION NO. : 10/533152
DATED : February 3, 2009
INVENTOR(S) : Carling et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 580 days Delete the phrase "by 580 days" and insert -- by 842 days --

Signed and Sealed this

Twenty-fourth Day of August, 2010

David J. Kappos
*Director of the United States Patent and Trademark Office*